(12) United States Patent
Venkatesh et al.

(10) Patent No.: US 8,133,506 B2
(45) Date of Patent: Mar. 13, 2012

(54) DRUG DELIVERY SYSTEMS COMPRISING WEAKLY BASIC DRUGS AND ORGANIC ACIDS

(75) Inventors: Gopi Venkatesh, Vandalia, OH (US); Jin-Wang Lai, Springborro, OH (US); Nehal H. Vyas, Huber Heights, OH (US); Vivek Purohit, East Lyme, CT (US)

(73) Assignee: Aptalis Pharmatech, Inc., Vandalia, OH (US)

( * ) Notice: Subject to any disclaimer, the term of this patent is extended or adjusted under 35 U.S.C. 154(b) by 0 days.

(21) Appl. No.: 12/209,285

(22) Filed: Sep. 12, 2008

(65) Prior Publication Data

US 2009/0232885 A1 Sep. 17, 2009

Related U.S. Application Data

(60) Provisional application No. 61/035,840, filed on Mar. 12, 2008.

(51) Int. Cl.
*A61K 9/48* (2006.01)
*A61K 9/16* (2006.01)
*A61K 31/4178* (2006.01)
(52) U.S. Cl. .................. 424/455; 424/497; 514/397
(58) Field of Classification Search ................ 424/455, 424/497; 514/397
See application file for complete search history.

(56) References Cited

U.S. PATENT DOCUMENTS

| | | | |
|---|---|---|---|
| 3,634,584 A | 1/1972 | Poole | |
| 3,917,813 A | 11/1975 | Pedersen | |
| 3,954,959 A | 5/1976 | Pedersen | |
| 4,083,949 A | 4/1978 | Benedikt | |
| 4,361,546 A | 11/1982 | Stricker et al. | |
| 4,367,217 A | 1/1983 | Gruber et al. | |
| 4,427,648 A | 1/1984 | Brickl et al. | |
| 4,438,091 A | 3/1984 | Gruber et al. | |
| 4,459,279 A | 7/1984 | Stricker et al. | |
| 4,578,264 A | 3/1986 | Stricker et al. | |
| 4,596,705 A | 6/1986 | Schepky et al. | |
| 4,663,150 A | 5/1987 | Panoz et al. | |

(Continued)

FOREIGN PATENT DOCUMENTS

EP 0032562 7/1981

(Continued)

OTHER PUBLICATIONS

West, Anthony R., Solid State Chemistry and its Applications, Wiley, New York, 1988, pp. 358 & 365.*

(Continued)

*Primary Examiner* — Robert A Wax
*Assistant Examiner* — Aradhana Sasan
(74) *Attorney, Agent, or Firm* — Cooley LLP (57) ABSTRACT

The present invention is directed to pharmaceutical compositions, and methods of making such compositions, wherein the compositions comprise a plurality of TPR and RR particles, wherein: the TPR particles each comprise a core coated with a TPR layer; the core comprises a weakly basic, poorly soluble drug and a pharmaceutically acceptable organic acid separated from each other by an SR layer; the RR particles each comprise the weakly basic, poorly soluble drug, and release at least about 80 wt. % of the weakly basic, poorly soluble drug in about 5 minutes when dissolution tested using United States Pharmacopoeia (USP) dissolution methodology (Apparatus 2—paddles@50 RPM and a two-stage dissolution medium at 37° C. (first 2 hours in 0.1N HCl followed by testing in a buffer at pH 6.8).

35 Claims, 6 Drawing Sheets

U.S. PATENT DOCUMENTS

| | | | |
|---|---|---|---|
| 4,716,040 | A | 12/1987 | Panoz |
| 4,721,619 | A | 1/1988 | Panoz et al. |
| 4,726,951 | A | 2/1988 | Panoz et al. |
| 4,820,521 | A | 4/1989 | Panoz et al. |
| 4,826,688 | A | 5/1989 | Panoz et al. |
| 4,863,742 | A | 9/1989 | Panoz et al. |
| 4,894,240 | A | 1/1990 | Geoghegan et al. |
| 5,320,853 | A | 6/1994 | Noda et al. |
| 5,705,190 | A | 1/1998 | Broad et al. |
| 5,840,329 | A | 11/1998 | Bai |
| 6,015,577 | A | 1/2000 | Eisert et al. |
| 6,596,311 | B1 | 7/2003 | Dobetti |
| 6,602,521 | B1 | 8/2003 | Ting et al. |
| 6,645,524 | B2 * | 11/2003 | Midha et al. .................. 424/459 |
| 6,702,803 | B2 | 3/2004 | Kupperblatt et al. |
| 2001/0046964 | A1 | 11/2001 | Percel et al. |
| 2003/0113374 | A1 | 6/2003 | Percel et al. |
| 2003/0170304 | A1 * | 9/2003 | Devane et al. ................ 424/469 |
| 2004/0019096 | A1 | 1/2004 | Andronis et al. |
| 2004/0258749 | A1 | 12/2004 | Guldner et al. |
| 2005/0232988 | A1 | 10/2005 | Venkatesh et al. |
| 2005/0238717 | A1 | 10/2005 | Fassihi et al. |
| 2005/0287211 | A1 * | 12/2005 | Yoshida et al. ............... 424/469 |
| 2006/0280795 | A1 | 12/2006 | Penhasi et al. |
| 2007/0190145 | A1 | 8/2007 | Venkatesh et al. |
| 2007/0196491 | A1 | 8/2007 | Venkatesh |

FOREIGN PATENT DOCUMENTS

| | | | |
|---|---|---|---|
| EP | 1 123 700 A1 * | 8/2001 | |
| WO | WO 02/36558 A2 | 5/2002 | |
| WO | WO 03/104192 A2 | 12/2003 | |
| WO | WO 2004/096182 A1 | 11/2004 | |
| WO | WO 2005/065640 A1 | 7/2005 | |
| WO | WO 2005/077341 A1 | 8/2005 | |

OTHER PUBLICATIONS

Young, Lee W., "International Search Report," 2 pages, from International Application No. PCT/US09/36787, filed Mar. 11, 2009, United States Patent and Trademark Office, Alexandria, Virginia, United States of America (mailed May 14, 2009).

Communication and annex from the European Patent Office Examining Division, issued Feb. 25, 2009 (EP07717476.1).

Communication and annex from the European Patent Office Examining Division, issued Mar. 6, 2009 (EP07717465.4).

International Preliminary Report on Patentability for PCT/US2007/061217, mailed Oct. 28, 2009.

International Preliminary Report on Patentability for PCT/US2007/061237, mailed Nov. 3, 2009.

International Search Report for International Application No. PCT/US2007/061237, mailed Sep. 7, 2007.

International Search Report for International Application No. PCT/US2007/061217, mailed Sep. 26, 2007.

Written Opinion of the International Searching Authority for PCT/US2007/061237, mailed Sep. 7, 2007.

Written Opinion of the International Searching Authority for PCT/US2007/061217, mailed Sep. 26, 2007.

Invitation to Respond to Written Opinion and Written Opinion issued Sep. 7, 2009, Singapore Patent Office.

Invitation to Respond to Written Opinion and Second Written Opinion issued Jan. 6, 2010, Singapore Patent Office.

Communication from the European Patent Office enclosing Third Party Observations in European application serial No. EP07717476.1, mailed Mar. 18, 2010.

Communication from the Intellectual Property Office of New Zealand for New Zealand Patent Application No. 569984, mailed on Mar. 16, 2010.

Communication from the Intellectual Property Office of New Zealand corresponding to New Zealand Patent Application No. 570039, mailed on Mar. 16, 2010.

Written Opinion of the International Searching Authority for PCT/US2009/036787, mailed May 14, 2009.

Venkatesh, Gopi, "Development of Controlled-Release SK&F 82526-J Buffer Bead Formulations with Tartaric Acid as the Buffer," Pharmacutical Development and Technology, 3(4), 477-485 (1998).

Sigma-Aldrich, Ondansetron hydrochloride dihydrate, O3639, p. 1, 2010.

Remington, The Science and Practice of Pharmacy, $21_{st}$ Ed., Chpt 46 pages 932-933 (2005).

Office Action from the Chinese Patent Office for Chinese Patent Application No. 200780011485.2 (Jun. 12, 2010) (translation).

Office Action from the Chinese Patent Office for Chinese Patent Application No. 200780011406.8 (Sep. 13, 2010) (translation).

International Preliminary Report on Patentability: PCT/US2009/036787 (Sep. 14, 2010).

Offical Action from the Russia Patent Office for Russian Patent Application No. 2008134912 (Sep. 22, 2010) (translation).

Offical Action from the Russia Patent Office for Russian Patent Application No. 2008134900 (Sep. 29, 2010) (translation).

Opposition Document filed in the Chilean Patent Department for Chilean Patent Application No. 598/2009 (translation).

* cited by examiner (FIG. 1.A)

Pilot PK Study

Dissolution: USP Apparatus 2 (Paddles at 50 RPM (700 mL of 0.1N HCl for first 2 hrs followed by testing at pH 6.8 by adding 200 mL of modified buffer

FIG. 10

T1: PF391EA001 (8 mg RR + 12 mg TPR with $T_{80}$ of 8 hrs
T2: PF392EA001 (8 mg RR + 16 mg TPR with $T_{80}$ of 8 hrs
T3: PF379EA001 (8 mg RR + 16 mg TPR with $T_{80}$ of 12 hrs
Reference: Zofran 8 mg (BID 8 hrs apart)

FIG. 11

DRUG DELIVERY SYSTEMS COMPRISING WEAKLY BASIC DRUGS AND ORGANIC ACIDS

CROSS-REFERENCE TO RELATED APPLICATION

The present application claims priority to U.S. Provisional Application No. 61/035,840 filed Mar. 12, 2008, which is incorporated herein by reference in its entirety for all purposes.

BACKGROUND OF THE INVENTION

In order to produce a desired pharmacological effect, a drug must be made available in appropriate concentrations at its site of action within the body. This availability is affected by numerous factors including the quantity of the drug administered, the rate of drug absorption, the distribution (binding or localization) within tissues, drug metabolism, and elimination from the body.

For orally administered drug dosage forms, drug absorption occurs within the gastrointestinal tract. While passing through the gastrointestinal tract, the drug should be released from the dosage form and be available in solution at or near the desired absorption site. The rate at which the drug is released from a dosage form and goes into solution is important to the kinetics of drug absorption. The dosage form and hence the drug is subjected to varying pHs during the transit, e.g., varying from about pH 1.2 (during fasting—but the stomach pH increases to as high as 4.0 after the consumption of food) to about 7.4 in other parts of the digestive tract (bile pH: 7.0-7.4 and intestinal pH: 5 to 7). Moreover, the transit time of the dosage form in different parts of the digestive tract may vary significantly depending on the size of the dosage form and prevailing local conditions. Other factors that influence drug absorption include physicochemical properties of the drug substance itself such as its pKa, solubility, crystalline energy, and specific surface area, as well as characteristics of the gastrointestinal tract itself, such as the properties of the luminal contents (pH, surface tension, volume, agitation and buffer capacity) and changes which occur following the ingestion of food. Consequently, it is often difficult to achieve drug release at constant rates.

Conventional oral dosage forms are often formulated as "immediate-release" dosage forms in which essentially the entire dose of drug is released from the dosage form within a very short period, e.g., minutes, following administration. Consequently, the plasma concentration of the drug typically rapidly rises to a peak concentration and subsequently declines as the drug is absorbed within tissues, metabolized, and/or excreted. The plasma concentration is generally characteristic of a particular drug due to the particular physical and metabolic properties of the drug. Generally, during some portion of the time period in which the plasma drug concentration rises, peaks and declines, the drug provides its therapeutic effects, i.e., when the plasma concentration of the drug reaches or exceeds the concentration required for clinical efficacy. If the plasma concentration is too high, undesirable side effects may occur, and when the plasma concentration of the drug drops below the clinically effective level, the therapeutic effects disappear.

Thus, in order to provide clinical efficacy while minimizing side effects it may be necessary to administer multiple doses of an immediate-release dosage form in order to maintain clinically effective plasma levels over the required period of time, while minimizing side effects due to excessive plasma levels.

Sustained or extended release dosage forms have been developed to minimize the number of doses administered in order to treat a particular condition. Sustained release dosage forms generally release the drug for an extended time period compared to an immediate-release dosage form. There are a number of different types of oral dosage forms that have been developed, including diffusion systems such as reservoir devices and matrix devices, dissolution systems such as encapsulated dissolution systems (including, for example, "tiny time pills") and matrix dissolution systems, combination diffusion/dissolution systems, osmotic systems and ion-exchange resin systems as described in Remington's Pharmaceutical Sciences, 1990 ed., pp. 1682-1685.

Basic and acidic drugs exhibit pH-dependent solubility profiles varying by more than 2 orders of magnitude in the physiological pH range. For example, the weakly basic serotonin 5-$HT_3$ receptor antagonist ondansetron hydrochloride is freely soluble in low pH gastric fluids, but it is practically insoluble at pH >6. Consequently, conventional once daily drug delivery systems such as matrix tablet formulations containing one or more dissolution rate controlling polymers or hydrophobic waxes, membrane coated monolithic or multiparticulate dosage forms, fail to release ondansetron in the relatively high pH environment of the intestinal tract, and are therefore unsuitable for once daily dosing.

Organic acids have been used to improve bioavailability, to reduce inter- and intra-subject variability, and to minimize food effects for weakly basic drugs. Multi-particulate dosage forms comprising weakly basic drugs to provide extended-release profiles are also described in the literature. These dosage forms are typically obtained by granulating or layering the drug with one or more organic acids and then coating the resulting particles with an extended release coating. However, such dosage forms are not suitable for once-daily dosing because they fail to maintain a sufficiently high plasma concentration of the drug, at least in part because the release of the organic acid is not sufficiently prolonged to provide enhanced dissolution of the weakly basic drug. Furthermore, in these compositions the weakly basic drugs can form varying levels of salts with the organic acids during processing and storage, which may affect the drug release properties.

SUMMARY OF THE INVENTION

The pharmaceutical compositions of the present invention provide improved drug release profiles for weakly basic, poorly soluble drugs, suitable for once daily dosing. The pharmaceutical compositions of the present invention provide a population of rapid release (RR) particles which quickly release the drug in the gastrointestinal tract, combined with a population of timed pulsatile release (TPR) particles which provide clinically effective plasma levels of the drug over an extended period, suitable for once daily dosing.

In one embodiment, pharmaceutical compositions of the present invention comprise a plurality of TPR and RR particles, wherein the TPR particles each comprise a core coated with a TPR layer; the core comprises a weakly basic, poorly soluble drug and a pharmaceutically acceptable organic acid separated from each other by an SR layer; the RR particles each comprise the weakly basic, poorly soluble drug, and release at least about 80 wt. % of the weakly basic, poorly soluble drug in about 5 minutes when dissolution tested using United States Pharmacopoeia (USP) dissolution methodology (Apparatus 2—paddles@50 RPM and a two-stage dissolution medium at 37° C. (first 2 hours in 0.1N HCl followed by testing in a buffer at pH 6.8).

In other embodiments, the TPR particles comprise an inert core (e.g. a sugar bead), sequentially coated with a pharmaceutically acceptable organic acid and a pharmaceutically acceptable binder; a sustained release (SR) layer (e.g., comprising a pharmaceutically acceptable water insoluble polymer, optionally plasticized with a pharmaceutically acceptable plasticizer); a drug layer comprising the weakly basic, insoluble drug and a pharmaceutically acceptable binder; an optional sealing layer (e.g. comprising a water soluble polymer); an optional second SR layer; and a TPR layer (e.g., comprising a water insoluble polymer, an enteric polymer, and an optional pharmaceutically acceptable plasticizer).

In still other embodiments, the RR particles comprise an inert core (e.g., sugar bead, optionally of smaller average diameter and the inert core of the TPR particles); coated with weakly basic, poorly soluble drug and a pharmaceutically acceptable binder.

In still other embodiments, the RR particles comprise the weakly basic, poorly soluble drug, granulated in the presence of a pharmaceutically acceptable polymeric binder, a pharmaceutically acceptable organic acid, and at least one excipient.

BRIEF DESCRIPTION OF THE DRAWINGS

FIG. 1.A illustrates the cross-section of an embodiment of a SR coated organic acid-containing particle.

FIG. 1.B illustrates a cross-section of an embodiment of a TPR particle comprising an SR coated organic acid-containing core.

DETAILED DESCRIPTION OF THE INVENTION

U.S. Provisional Application No. 60/762,750 filed Jan. 27, 2006, U.S. Provisional Application No. 60/762,766 filed Jan. 27, 2006, U.S. application Ser. No. 11/668,167, filed Jan. 29, 2007, and U.S. application Ser. No. 11/668,408, filed Jan. 29, 2007, are each incorporated herein by reference in their entirety for all purposes.

The above applications, and all other documents cited herein are incorporated by reference in their entirety for all purposes. The citation of any document is not to be construed as an admission that it is prior art with respect to the present invention.

The term "weakly basic, poorly soluble drug" refers to a basic drug, pharmaceutically acceptable salts, polymorphs, solvates, esters, stereoisomers and mixtures thereof. "Weakly basic" refers to drugs which are freely to moderately soluble at acidic pHs, but are poorly to practically insoluble at neutral and alkaline pHs, and have pKa values in the range of about 5 to 14. For example ondansetron hydrochloride contains an α-hydroxyl secondary amine with a pKa of 7.4. The pH-dependent solubility data for exemplary weakly basic drugs are presented in Table 1, below. For example, ondansetron hydrochloride is freely soluble at a pH of less than 2, but has a solubility of less than 50 μm/mL at a pH of 6.8 or higher. Iloperidone has a solubility in 0.1N HCl (hydrochloric acid) of about 3 mg/mL, but at pH 6.8 has a solubility of only about 30 μg/mL. Clonazepam is practically insoluble at physiological pHs.

Table 1 lists the solubility enhancement of weakly basic drugs in organic acid buffers. Three distinct groups can be identified. Group A drugs, as represented by ondansetron hydrochloride, exhibit a dramatic increase in solubility of the weakly basic drug in a buffer with a trace of fumaric acid. For example, the solubility of ondansetron of about 26 mg/mL in a buffer containing only 0.05 mg/mL of fumaric acid remains unchanged upon increasing the concentration of fumaric acid in the buffer up to 5 mg/mL. For Group B drugs, represented by iloperidone, carvedilol and lamotrigine, the solubility of the weakly basic drug increases with increasing concentration of the organic acid. Furthermore, the solubilization capability of organic acids varies widely. For Group C drugs, represented by clonazepam, the addition of an organic acid has very limited impact, i.e., the solubility enhancement amounts typically to less than 3-fold. For example, the solubility of clonazepam is about 11.6 and 6.9 μg/mL in buffers at pH 2.3 and 6.8 containing a higher and lower concentration of fumaric acid, respectively.

TABLE 1

| Solubility Profiles of Weakly Basic Drugs | | | | | |
|---|---|---|---|---|---|
| Solubility of Ondansetron HCl in Aqueous Buffer | | Solubility of Iloperidone in Aqueous Buffer | | Solubility of Clonazepam in Aqueous Buffer | |
| pH | mg/mL | pH | mg/mL | pH | mg/mL |
| 1.0 | > | 1.2 | 3.90 | 2.2 | 0.0114 |
| 2.20 | 23.3 | 3.01 | 1.437 | 2.8 | 0.0102 |

TABLE 1-continued

Solubility Profiles of Weakly Basic Drugs

| 3.20 | 25.7  | 3.06 | 0.917 | 3.2 | 0.0096 |
|------|-------|------|-------|-----|--------|
| 4.20 | 10.9  | 4.08 | 0.681 | 3.8 | 0.0092 |
| 5.00 | 3.6   | 4.46 | 0.586 | 4.2 | 0.0091 |
| 5.60 | 1.7   | 5.09 | 0.341 | 4.8 | 0.0086 |
| 6.20 | 0.4   | 6.11 | 0.117 | 5.4 | 0.0084 |
| 6.80 | 0.036 | 7.02 | 0.011 | 6.2 | 0.008  |
| 7.00 | 0.025 |      |       |     |        |

| Concentration of Fumaric Acid | | Solubility of Ondansetron HCl in Fumaric Acid | | Solubility of Clonazepam in Fumaric Acid | |
|---|---|---|---|---|---|
| mg/mL | pH | mg/mL | pH | mg/mL | |
| 5.0    | 2.01 | 26.9 | 2.3  | 0.0116 |
| 2.5    | 2.14 | 27.0 | 2.8  | 0.0103 |
| 1.0    | 2.40 | 26.1 | 3.2  | 0.0096 |
| 0.25   | 2.75 | 26.2 | 3.7  | 0.0098 |
| 0.05   | 3.49 | 26.0 | 5.50 | 0.29   |
| 0.01   | 4.05 | 26.1 |      |        |
| 0.0025 | 4.33 |      |      |        |

| Fumaric Acid | | Aspartic Acid | | Glutamic Acid | |
|---|---|---|---|---|---|
| pH | mg/mL | pH | mg/mL | pH | mg/mL |
| 2.4 | 1.15 | 2.85 | 9.30 | 3.07 | 5.95 |
| 2.8 | 0.72 | 3.40 | 5.52 | 3.41 | 5.16 |
| 3.2 | 0.46 | 3.89 | 3.79 | 3.80 | 3.26 |
| 4.0 | 0.19 | 4.52 | 1.37 | 4.40 | 1.70 |
| 5.0 | 0.19 | 5.57 | 0.15 | 5.50 | 0.29 |
| 6.1 | 0.03 |      |      |      |      |

In one embodiment, "weakly basic, poorly soluble drug" refers to a nitrogen (N)-containing selective serotonin 5-HT$_3$ antagonist having a pKa in the range of from about 5 to 14 and a solubility of not more than 200 μg/mL at a pH of 6.8 and a ratio of optimal highest dose to solubility at pH 6.8 of not less than about 100. In other embodiments, the selective serotonin 5-HT$_3$ antagonist is selected from the group consisting of ondansetron, tropisetron, granisetron, dolasetron, and palonosetron, and includes pharmaceutically acceptable salts, solvates, esters, stereoisomers, and mixtures thereof.

Ondansetron is indicated for the prevention of nausea and vomiting associated with radiotherapy and/or chemotherapy and prevention of postoperative nausea and/or vomiting. Zofran® Tablets (Ondansetron HCl dihydrate, 4, 8, and 24 mg base equivalent) are commercially available. Ondansetron is administered 8 mg "bid" for chemotherapy and 8 mg "tid" for radiotherapy. A once-daily dosing of ondansetron hydrochloride is commercially desirable and would simplify the dosing regimen and enhance patient compliance. Ondansetron exists as a racemate and it contains an α-hydroxyl secondary amine, with a pKa of 7.4. Ondansetron HCl exhibits a pH-dependent solubility profile (solubility decreasing by 2-3 orders of magnitude as the pH increases). Ondansetron is well absorbed from the gastrointestinal tract and undergoes some first-pass metabolism. The elimination half-life averages approximately 3.8±1 hrs. Since the drug dissolution is the rate-limiting factor for absorption in the distal part of the GI tract potentially due to the decrease in solubility, the once-daily dosage form in accordance with one embodiment would comprise at least two bead populations—one IR or RR particle population and another TPR particle population.

The term "TPR particle" or "TPR bead" refers to a drug-containing particle, e.g., a drug-layered bead, drug-containing granulate, or drug particle, coated with a TPR ("timed pulsatile release") coating. The TPR coating provides an immediate release pulse of the drug, or a sustained drug-release profile after a pre-determined lag time. The term "lag-time" refers to a time period immediately after administration of the drug-containing particle wherein less than about 10%, more particularly substantially none, of the drug is released from a particle. In some embodiments, a lag-time of from at least about 2 to 10 hours is achieved by coating the particle with, e.g. a combination of at least one water-insoluble polymer and at least one enteric polymer (e.g., a combination of ethylcellulose and hypromellose phthalate). The TPR layer can optionally contain a plasticizer.

The term "SR layer" refers to a layer providing sustained release properties, e.g. a layer which slows the release of the drug from the drug-containing particle but does not provide an appreciable "lag-time". An SR layer or coating comprises e.g. a water-insoluble polymer such as ethylcellulose.

As used herein, the term "immediate release" or IR refers to release of greater than or equal to about 50% (especially if taste-masked for incorporation into an orally disintegrating tablet dosage form), in some embodiments greater than about 75%, in other embodiments greater than about 90%, and in accordance with certain embodiments greater than about 95% of the active within about 2 hours, for example within about one hour following administration of the dosage form. The term can also refer to the release of the active from a timed, pulsatile release dosage form characterized by an immediate release pulse after the designed lag time. As used herein, as well as in specific examples thereof, the term "RR (rapid release) drug particles" includes drug layered 45-60 mesh, in other embodiments 60-80 mesh sugar spheres and water-soluble lactose and fumaric acid containing microgranules comprising said drug designed to provide dissolution profiles similar to that of a reference drug product (for example, in the case of ondansetron HCl, RR drug particles and Zofran® having similar dissolution profiles).

The clinical terms, 'plasma concentration—time profile, $C_{max}$, AUC, $T_{max}$, elimination half life' have their generally accepted meanings, and hence, are not redefined. Unless indicated otherwise, all percentages and ratios are calculated by weight based on the total composition.

Dissolution testing of IR beads, whether taste-masked or not, is conducted with a USP Apparatus 1 (baskets at 100 rpm) or Apparatus 2 (paddles at 50 rpm) in 900 mL of 0.1N HCl at 37° C. while the dissolution testing of SR and TPR beads is conducted in a USP apparatus using a two-stage dissolution medium (first 2 hours in 700 mL of 0.1N HCl at 37° C. followed by dissolution testing at pH=6.8 obtained by the addition of 200 mL of a pH modifier). Drug/acid-release with time is determined by HPLC on samples pulled at selected intervals.

There are instances wherein the onset of drug release should begin several hours following oral administration to provide adequate plasma concentration to be suitable for a once-daily dosing regimen, depending on the elimination half-life of the active. In accordance with particular aspects of the invention, drug release may be delayed for up to about 8-10 hours after oral administration.

Figure 1:
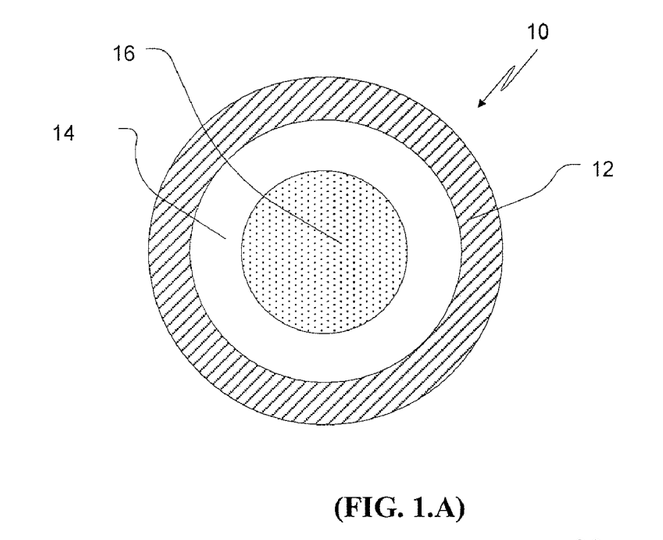

Specific embodiments of the invention will be described in further detail with reference to the accompanying FIGS. 1.A and 1.B. In FIG. 1.A, an SR-coated core 10 comprising an SR coating 12 applied on an organic acid-containing particle comprising a layer of a pharmaceutically acceptable organic acid in a binder 14 coated on an inert particle core 16. The inert particle core 16, organic acid-coating layer 14 and a dissolution rate controlling SR layer 12 make up the SR-coated organic acid-containing particle 10. In FIG. 1.B, a representative TPR particle is illustrated. The TPR bead 20 comprises a lag-time coating 22 applied on a primary SR layer 24, a protective seal-coat 26 and a weakly basic drug layer 28 applied on an SR-coated acid-containing particle 10. In certain embodiments of the present invention, the intermediate SR barrier layer is not applied, i.e., the TPR layer is directly applied over the seal coated IR particle.

The weakly basic drug is typically applied from a polymeric binder solution. The SR coating sustains the drug release while the lag-time coating provides the lag-time (a time period exhibiting less than about 10%, more particularly substantially none, of the dose released). Thus the lag-time coating 22, outer SR coating (if present) on the IR beads 24, and inner SR coating 12 on the acid-containing core together control the release properties of both the drug and acid from the TPR beads.

The weakly basic, poorly soluble drug can be in the form of drug crystals, amorphous drug particles, granules (e.g., drug granulated with one or more excipients) or combinations thereof. Alternatively, the drug can be layered on to an inert core, or on an inert core coated with other components of the composition, e.g., or a pharmaceutically acceptable organic acid and/or one or more sealant or SR layers as defined herein. In one embodiment, the drug is layered onto an inert core (e.g. as described herein) which has been first coated with a pharmaceutically acceptable organic acid, and then coated with an SR layer (e.g. as described herein). In other embodiments, the drug is first coated onto an inert core, and then sequentially coated with an SR layer and a pharmaceutically acceptable acid layer. In still other embodiments, particles of the drug itself (e.g. crystalline and/or amorphous) are sequentially coated with an SR layer and a pharmaceutically acceptable acid layer.

In one embodiment, the inert core may be a sugar sphere, a cellulose sphere, a silicon dioxide sphere, mannitol-microcrystalline cellulose sphere or the like, with a suitable particle size distribution (for example 20-25 mesh sugar spheres and 60-80 mesh sugar spheres or 100-200 μm cellulosic spheres for RR particles).

When the drug is layered onto the inert core, or a coated inert core, the drug can be dissolved in a suitable solvent and coated using various methods, for example, fluid bed coating processes. Alternatively, the drug can be combined with a pharmaceutically acceptable binder, and layered onto the core. An aqueous or a pharmaceutically acceptable solvent medium may be used for preparing core particles based on coated inert particles. The type of inert binder that is used to bind the water-soluble organic acid or weakly basic drug to the inert particle or to the SR coated acid-containing core is not critical, but usually comprises water soluble or alcohol soluble binders such as polyvinylpyrrolidone (PVP or povidone), copolymers of polyvinylpyrrolidone and vinyl alcohol, copolymers of polyvinylpyrrolidone and vinyl acetate, copolymers of polyvinylpyrrolidone with vinyl chloride, copolymers of polyvinylpyrrolidone with vinyl butyrate, copolymers of polyvinylpyrrolidone with vinyl laurate, copolymers of polyvinylpyrrolidone with vinyl stearate, hydroxypropylcellulose, or hypromellose (HPMC), hydroxypropyl methylcellulose (HPMC), hydroxypropylcellulose, carboxyalkylcelluloses, polyethylene oxide, polysaccharides such as dextran, starches such as corn starch, acacia, carboxymethylcellulose, gelatin, etc., which may be dissolved or dispersed in water, alcohol, acetone or mixtures thereof. The binder may be used at any concentration capable of being applied to the inert particle. Typically, the binder is used at a concentration of about 0.5 to 10% by weight. The organic acid or the weakly basic drug may be preferably present in this coating formulation in solution form. The drug concentration may vary depending on the application but typically will be used at concentrations from about 5 to 30% by weight depending on the viscosity of the coating formulation.

In other embodiments, the particle may comprise an organic acid (e.g., fumaric acid) crystal with a desired mean particle size, coated with a water-insoluble polymer (or the combination of a water-insoluble polymer and a water soluble or enteric polymer), then coated with a drug layer such that the acid release is slower than or synchronized with the drug dissolution/release from the particle, thereby ensuring that the acid release is not complete prior to depletion of the drug.

In accordance with other embodiments, the drug-containing cores may be prepared by rotogranulation, or by granulation followed by extrusion-spheronization or tableting into micro-tablets. The organic acid, a binder, and optionally other pharmaceutically acceptable excipients (e.g., diluents/fillers) may be blended together in a high-shear granulator, or a fluid bed granulator, such as a Glatt GPCG granulator, and granulated to form agglomerates. The wet mass can be extruded and spheronized to produce spherical particles (pellets). The blend comprising acid particles, a binder and optionally a filler/diluent or drug-containing granules can also be compressed into micro-tablets (about 1-1.5 mm in diameter) to produce organic acid-containing pellets. In these embodiments, the acid content could be as high as 95% by weight based on the total weight of the granulated, extruded or compressed core. These acid-containing cores are coated with an SR membrane prior to drug-layering and subsequent coating with functional polymers.

The TPR particles of the present invention include a layer comprising a pharmaceutically acceptable acid, separated from the drug-containing layer by an SR layer. The SR layer comprises a water-insoluble polymer.

Representative pharmaceutically acceptable organic acids which enhance the solubility of the drug include citric acid, fumaric acid, malic acid, maleic acid, tartaric acid, succinic acid, oxalic acid, aspartic acid, glutamic acid and the like. The ratio of organic acid to drug varies from about 5:1 to 1:10 by weight, including 5:1, 4:1, 3:1, 2:1, 1:1, 1:2, 1:3, 1:4, 1:5, 1:6, 1:7, 1:8, 1:9, and 1:10.

The solubility enhancing property of organic acid buffers is taken advantage of, and at the same time, the in situ formation of acid addition compounds is prevented by having an SR layer between the inner organic acid layer and the weakly basic drug layer. The SR layer precisely controls the release of the organic acid so as to insure no drug is left behind in the dosage form for lack of solubilizing acid in the TPR particle.

Representative examples of water-insoluble polymers useful in the SR layer include ethylcellulose, polyvinyl acetate (for example, Kollicoat SR#30D from BASF), cellulose acetate, cellulose acetate butyrate, neutral copolymers based on ethyl acrylate and methylmethacrylate, copolymers of acrylic and methacrylic acid esters with quaternary ammonium groups such as Eudragit® NE, RS and RS30D, RL or RL30D and the like.

The water-insoluble polymer of the SR layer may be further plasticized with one or more pharmaceutically acceptable plasticizers. Representative examples of plasticizers include triacetin, tributyl citrate, triethyl citrate, acetyl tri-n-butyl citrate diethyl phthalate, castor oil, dibutyl sebacate, acetylated monoglycerides and the like or mixtures thereof. The plasticizer, when used, may comprise about 3 to 30 wt. % and more typically about 10 to 25 wt. % based on the polymer. The type of plasticizer and its content depends on the polymer or polymers and nature of the coating system (e.g., aqueous or solvent based, solution or dispersion based and the total solids).

The pharmaceutically acceptable acid-containing layer can then be coated with an optional second SR coating, a seal coating (e.g., hypromellose), and/or a TPR layer comprising a pharmaceutically acceptable water insoluble polymer (e.g. as described herein), combined with one or more water-soluble or enteric polymers.

Representative examples of water-soluble polymers useful in the invention include polyvinylpyrrolidone (PVP), hydroxypropyl methylcellulose (HPMC), hydroxypropylcellulose (HPC), polyethylene glycol, and the like.

Representative examples of enteric polymers useful in the invention include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methylmethacrylate copolymers and shellac. These polymers may be used as a dry powder or an aqueous dispersion. Some commercially available materials that may be used are methacrylic acid copolymers sold under the trademark Eudragit® (L100, S100, L30D) manufactured by Rohm Pharma, Cellacefate® (cellulose acetate phthalate) from Eastman Chemical Co., Aquateric® (cellulose acetate phthalate aqueous dispersion) from FMC Corp. and Aqoat® (hydroxypropyl methylcellulose acetate succinate aqueous dispersion) from Shin Etsu K.K.

An aqueous or a pharmaceutically acceptable solvent medium may be used for preparing organic acid-containing core particles for drug layering, viz., acid-containing beads by layering an acid onto inert cores (e.g., sugar spheres), or IR beads by drug-layering onto acid-containing cores or directly onto sugar spheres from an appropriate polymer binder solution in fluid-bed equipment. Also, an aqueous dispersion of functional polymers, which are available as dispersions or a solvent system may be used for dissolving functional polymers for coating acid-containing beads, IR beads or SR beads.

In general, it is desirable to prime the surface of the drug-layered particles before applying the barrier-membrane coatings or to separate the different membrane layers by applying a thin hydroxypropyl methylcellulose (HPMC) (e.g., Pharmacoat 603 or Opadry® Clear) film. While HPMC is typically used, other primers such as hydroxypropylcellulose (HPC) or lower viscosity ethylcellulose can also be used. Any of the coatings described herein can be applied using any of the coating techniques commonly used in the pharmaceutical industry, but fluid bed coating is particularly useful.

The individual coatings on the acid-containing cores and IR beads will vary from about 5 to 50% by weight depending on the relative solubility of organic acid to drug, nature of the drug, composition of the coating, and the required lag-time. In one embodiment, the acid and drug-containing TPR particles may be provided with a SR coating of a plasticized water-insoluble polymer, such as ethylcellulose (EC-10), at about 5-50% by weight to sustain the acid release over about 5-20 hours. In certain other embodiments, the acid and drug-containing particles may be provided with a TPR coating of a plasticized ethylcellulose and hydroxypropyl methylcellulose (hypromellose) phthalate (HP-55) at about 10-50% by weight, while the IR beads are coated with ethylcellulose (EC-10) at 5-20% by weight to achieve the drug-release synchronized with that of the acid. In yet another embodiment of the present invention, the IR beads may not be provided with any barrier coating, and the outer TPR coating of EC-10/HP-55/plasticizer at about 45.5/40/14.5 for a weight gain of about 30-50% by weight controls the drug-release following the lag-time. The composition of the coating layer and the individual weights of the polymers are important factors to be considered for achieving a desired drug/acid-release profile and lag time prior to appreciable drug release.

In one embodiment, the active core of the dosage form of the present invention may comprise an inert particle coated with an organic acid, an SR coating, drug-layered (IR beads), further barrier or SR coated and/or lag-time coated. The amount of organic acid and the drug-load in the core will depend on the drug, the dose, its pH-dependent solubility, solubility enhancement, and elimination half-life. Those skilled in the art will be able to select an appropriate amount of drug/acid for coating onto the core and apply an SR coating of appropriate thickness prior to drug layering and further functional polymer coating to program the acid release, which, in accordance with certain embodiments, is synchronized with that of the drug to ensure complete release of the drug prior to depletion of the acid from TPR beads.

In specific embodiments, the drug is layered onto SR coated fumaric acid-containing beads (e.g., a sugar bead coated with a fumaric acid-containing layer). The drug (e.g., ondansetron) and a polymeric binder (e.g., povidone) solution are coated onto the SR coated fumaric acid-containing bead, and subsequently coated with a protective seal-coat comprising a hydrophilic polymer such as Pharmacoat 603 (Hypromellose 2910 3 cps) or Opadry® Clear, to form IR beads. In one embodiment, the drug-containing IR beads may be coated twice—an inner barrier coating membrane with a water-insoluble polymer (e.g., ethylcellulose) alone or in combination with a water-soluble polymer and a lag-time coating of a water-insoluble polymer in combination with an enteric polymer to produce TPR beads with a lag-time (release with a delayed-onset) of approximately 1 to 10 hours upon oral administration. The water-insoluble polymer and enteric polymer may be present at a weight ratio of from about 9:1 to about 1:4, for example at a weight ratio of from about 3:1 to 1:1. The coating typically comprises from about 5% to about 60%, for example from about 10% to about 50% by weight of the coated beads. In accordance with yet another embodiment, the IR beads may simply be coated with a combination of a water-insoluble polymer and an enteric polymer in the aforementioned amounts.

If an initial rapid release of drug is desired, the dosage forms of the present invention can comprise a combination of TPR and IR and/or RR particles, where the IR and/or RR particles provide an initial rapid release of the drug, and the sustained release is provided by the TPR particles. In some embodiments, the dosage forms of the present invention comprise a combination of TPR and IR beads, and in other embodiments, the dosage forms of the present invention comprise combinations of TPR and RR particles, or combinations of TPR, IR, and RR particles.

As described herein IR particles release greater than about 50% of the drug within about two hours of dosing. RR particles are a particular type of immediate release particle having a significantly higher rate of release of the drug compared to IR particles, for example, releasing at least about 80% of the drug within about fifteen minutes when dissolution tested using United States Pharmacopoeia (USP) dissolution methodology (Apparatus 2—paddles@50 RPM and a two-stage dissolution medium at 37° C. (first 2 hours in 0.1N HCl followed by testing in a buffer at pH 6.8). In one embodiment, the RR particles comprise the weakly basic, poorly soluble drug layered onto small particle size inert cores, such as 60-80 mesh sugar spheres. In other embodiments, the RR particles comprise the drug granulated with at least one water soluble excipient such as lactose and at least one organic acid such as fumaric acid. Both of the types of ondansetron-containing RR particles described above show rapid dissolution similar to that of reference drug product, Zofran® IR Tablets, 8 mg under a discriminating in vitro dissolution method using USP Apparatus 2 in 500 mL buffer at pH 6.8.

Thus, in one embodiment, the multiparticulate pharmaceutical compositions of the present invention comprise rapid release drug particles (e.g., drug layered beads comprising 60-80 mesh sugar spheres or granules) and one or more TPR particle populations. In some embodiments, the multiparticulate pharmaceutical compositions of the present invention, containing RR and TPR particle populations release the drug and acid at similar rates. In other embodiments, such compositions release the acid more slowly than the drug to avoid undissolved drug being left behind inside the TPR particles.

In particular embodiments, the multiparticulate pharmaceutical compositions of the invention comprise rapid release drug particles and one or more TPR coated bead populations of a selective serotonin 5-$HT_3$ blocking agent, wherein the TPR bead comprises:
  a) an organic acid-containing core particle (organic acid crystal, pellet, bead and the like);
  b) a barrier or sustained-release membrane on the acid-containing core particle comprising a water-insoluble polymer or a water-insoluble polymer in combination with a water-soluble or enteric polymer;
  c) a weakly basic drug layered on the barrier-coated acid-containing core particle and optionally provided with a protective seal-coat to form an immediate-release (IR) bead;
  d) if providing SR beads, an SR coating membrane on the IR bead comprising a water-insoluble polymer or a water-insoluble polymer in combination with a water-soluble polymer forming an SR bead; and/or
  e) if providing TPR beads, a lag-time coating membrane on the SR-coated bead of step d, or directly on the IR bead of step c, comprising a combination of a water-insoluble and enteric polymers to form a timed, pulsatile-release (TPR) bead.

The compositions of the TPR bead populations in accordance with particular aspects of the invention typically exhibit desired or target release profiles of both the drug and organic acid following a pre-determined lag-time of at least 2 hours when tested for drug and/or organic acid release using the 2-stage dissolution methodology described herein.

A pharmaceutical composition of a selective serotonin 5-$HT_3$ blocking agent with a solubility of not more than about 200 μg/mL at pH 6.8, and a ratio of optimal highest dose to solubility at pH 6.8 of not less than about 100, such as ondansetron hydrochloride dihydrate, may be prepared by filling TPR and RR bead populations into a hard gelatin capsule or compressing into a conventional tablet.

In accordance with particular aspects of the present invention, the pharmaceutical multiparticulate dosage form may comprise RR drug particles, a first TPR bead population, and an SR bead population or a second TPR bead population. In certain embodiments, the ratio of RR drug particles to the first TPR bead population to the SR bead or second TPR bead population may vary from about 10:90:0 to about 40:10:50.

The present invention also provides a method for manufacturing a multiparticulate dosage form comprising rapid release drug particles and one or more timed, pulsatile release bead populations or one or more weakly basic actives comprising SR-coated organic acid-containing cores, i.e., a well time-controlled series of pulses so that the active agents and the acid, being deposited in well separated/isolated layers of the TPR bead, do not come into contact with each other to form acid-addition compounds until the dosage form comes into contact with a dissolution medium or body fluids following oral ingestion. The dosage form thus produced exhibits composite release profiles of the drug and the acid that are comparable, more particularly, the acid-release profile is slower than that of the drug so that no undissolved drug is left behind in the dosage form for lack of solubilizing organic acid.

In accordance with one embodiment of the present invention, the method of preparing once daily dosage forms comprising TPR beads may include the steps of:
  a. providing an organic acid-containing core particle (e.g., an organic acid crystal with a desired particle size distribution or a particle comprising an inert particle (e.g., a sugar sphere, a cellulose sphere, a mannitol-microcrystalline cellulose sphere, or a silicon dioxide sphere) layered with an organic acid from a polymeric binder solution);
  b. coating the organic acid-containing core particle with an SR coating membrane consisting of a water-insoluble polymer such as EC-10 (ethylcellulose with a mean viscosity of 10 cps) alone or in combination with a water-soluble polymer (e.g., povidone or PEG 400) or an enteric polymer such as hydroxypropyl methylcellulose phthalate (e.g., HP-55);
  c. applying a layer of a weakly basic drug such as ondansetron hydrochloride dihydrate onto the SR coated organic acid-containing core particle and further applying a protective seal-coat of Pharmacoat 603 or Opadry® Clear to form an IR bead;
  d. optionally applying a barrier coating membrane onto the IR bead with a solution of a water-insoluble polymer (e.g., ethylcellulose) alone or in combination with a water-soluble polymer (e.g., polyethylene glycol, PEG 400) to produce an SR bead; and
  e. applying a lag-time coating membrane onto the SR bead of step d, or directly on the IR bead of step c, with a solution of a water-insoluble polymer in combination with an enteric polymer (e.g., ethylcellulose and hypromellose phthalate) at a ratio of about 10:1 to 1:4 to form a timed pulsatile-release drug particle (TPR) bead in accordance with the disclosures in the co-pending U.S. patent application Ser. No. 11/120,139 filed May 2, 2005. U.S. patent application Ser. No. 11/668,167 with a priority date of Jan. 27, 2006; U.S. patent application Ser. No. 11/668,408 with a priority date of Jan. 27, 2006. U.S. patent application Ser. No. 11/847,219 with a priority date of Aug. 31, 2006; U.S. Pat. No. 6,500,454, U.S. Pat. No. 6,627,223, U.S. Pat. No. 6,663,888, and U.S. Pat. No. 7,048,945 each of which is hereby incorporated by reference in its entirety for all purposes.
  f. filling RR drug particles (as described herein) and one or more TPR bead populations into hard gelatin capsules or compressing into conventional tablets exhibiting composite plasma profiles suitable for a once-daily dosing regimen with reduced incidence of adverse events including non-compliance.

The present invention is also directed to multi-dose forms, i.e., drug products in the form of multi-particulate dosage forms (e.g., hard gelatin capsules or conventional tablets prepared using a rotary tablet press) comprising one or more bead populations for oral administration to provide target PK profiles in patients in need of treatment. The conventional tablets rapidly disperse on entry into the stomach. The one or more coated bead populations may be compressed together with appropriate excipients into tablets (for example, a binder, a diluent/filler, and a disintegrant for conventional tablets.

In some embodiments, IR and RR (immediate and rapid release) beads for incorporation into finished dosage forms are prepared by layering said drug from a polymer binder solution onto medium size inert cores used for preparing SR and/or TPR beads and small particle size inert ores such as 45-60 mesh, or specifically onto 60-80 mesh inert cores, respectively. Alternatively, RR particles with an average particle size of not more than 400 μm may be prepared by granulating said drug, a water soluble excipient such as lactose and an organic acid.

The following non-limiting examples illustrate the drug delivery dosage forms as capsules or conventional tablets, comprise a rapid release pulse similar to that of the reference product. Such compositions maintain a drug plasma concentration at a level which provides an acceptable clinical benefit, and minimizes the occurrence of side-effects associated with $C_{max}$ or $C_{min}$.

EXAMPLE 1

1.A Fumaric Acid-Containing Cores: Hydroxypropyl cellulose (Klucel LF, 23.9 g) was slowly added to denatured SD 3C 190 proof alcohol while stirring rigorously to dissolve and then fumaric acid (215.4 g) was slowly added to dissolve. A Glatt GPCG 5 equipped with a 9" bottom spray Wurster insert, 10" partition column and 16 mm tubing was charged with 3750 g of 25-30 mesh sugar spheres. The sugar spheres were layered with the fumaric acid solution while maintaining the product temperature at about 33-34° C. and inlet air velocity at flap opening of 38%. The acid cores were dried in the unit for 10 min to drive off residual solvent/moisture and sieved through 20-30 mesh screens.

1.B SR-coated Fumaric acid Cores: The fumaric acid cores (3750 g) from above were coated with a solution of EC-10 and PEG 400 dissolved in 98/2 acetone/water (6% solids) for a weight gain of 10% by weight at two ratios, viz., (B.1) 60/40 and (B.2) 75/25 to examine its effect on the drug release from SR and TPR beads. The processing conditions were as follows: atomization air pressure: 2.0 bar; nozzle diameter: 1.0 mm; bottom air distribution plate: 'B' with 15 gauge 100 mesh screen; spray/shake interval: 30 s/3 s; product temperature maintained at 35±1° C.; inlet air volume: 155-175 cfm (cubic meters per second), and spray rate increased from 8 to 30 g/minute;

1.C Ondansetron Hydrochloride IR Beads: Povidone (PVP K-29/32, 19.5 g) was slowly added to 50/50 water/Denatured Alcohol 3C, 190 Proof (3699.4 g) while mixing to dissolve. Ondansetron hydrochloride dihydrate (175.2 g) was slowly added to the binder solution to dissolve the drug. SR-coated acid cores (3700 g) obtained from B.1 and B.2 above were coated in the Glatt GPCG 5 with the drug solution (5% solids), while maintaining the product temperature at 36±1° C.; and inlet air volume at 60-65 cfm and spray rate being increased from about 20-25 g/min. The drug-layered beads were provided with a protective seal-coat of Pharmacoat® 603 (hypromellose 2910; 3 cps) (2% weight gain) to form IR beads.

1.D Ondansetron Hydrochloride SR Beads: Ondansetron hydrochloride IR beads (3700 g) from above were barrier-coated (SR coated) by spraying a solution (7.5% solids) of 90/10 EC-10/TEC (triethyl citrate) at 5 and 10% by weight and dried in the Glatt for 10 minutes to drive off excess residual solvent. The dried beads were sieved to discard any doubles if formed.

1.E Ondansetron Hydrochloride TPR Beads: Ondansetron hydrochloride SR beads (3500 g) from Example 1D were further coated with a lag-time coating membrane of EC-10/HP-55/TEC (triethyl citrate) at a ratio of 45.5/40.0/14.5 for a weight gain of about 30%, 40% and 50%. The TPR beads were dried in the Glatt at the same temperature to drive off residual solvent and sieved.

Figure 2:
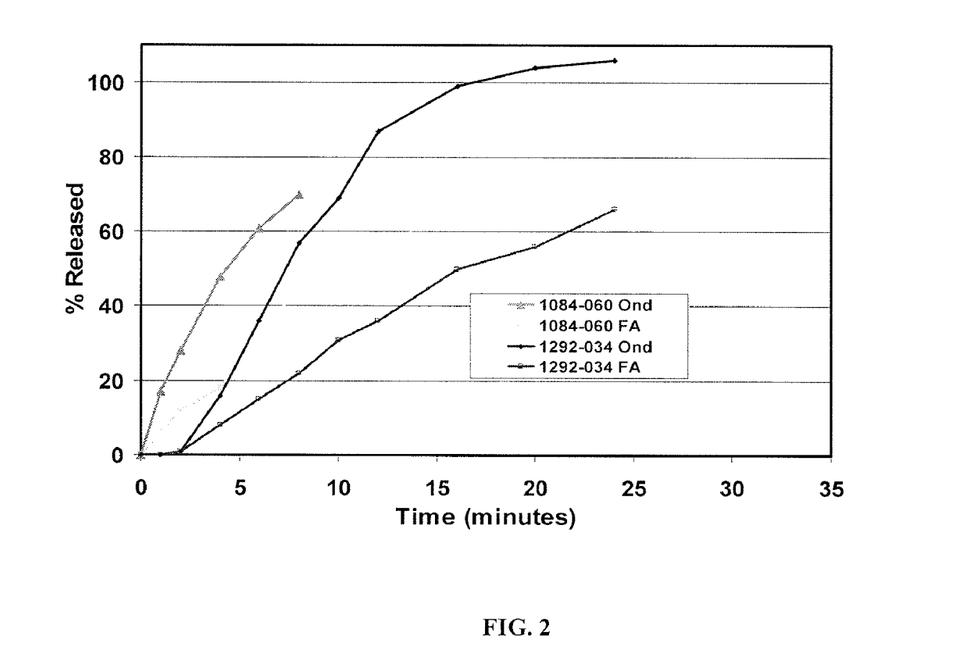
FIG. 2 shows the release profiles of both fumaric acid and ondansetron hydrochloride from SR particles (Lot#1084-060-IR beads drug layered on fumaric acid-containing cores coated with 60/40 EC-10/PEG 400, 10 wt. %, of Example 1) and from TPR beads (Lot#1292-034-IR beads drug layered on fumaric acid-containing cores coated with 75/25 EC-10/PEG 400, 5 wt. %) coated with EC-10/HP-55/TEC at a ratio of 63/22/15, 15 wt. %, of Example 6).

FIG. 2 shows the synchronized release profiles achieved for fumaric acid and ondansetron from SR beads (Lot#1084-060-IR beads coated with 60/40 EC-10/PEG 400 at 10% by weight on fumaric acid-containing cores coated with 75/25 EC-10/PEG 400 at 10%) and from TPR beads (Lot#1292-034-IR beads layered on fumaric acid-containing cores coated with 75/25 EC-10/PEG 400 at 10%) coated with EC-10/HP-55/TEC at a ratio of 63/22/15 for a weight gain of 15% by weight (prepared as described in Example 6, below). The fumaric acid release is significantly slower than that of ondansetron, thereby ensuring that no ondansetron is left behind inside the coated bead due to exhaustion of the fumaric acid.

EXAMPLE 2

2.A Fumaric Acid-Containing Cores: Fumaric acid-containing cores were prepared by the procedure described in Example 1.A excepting that 90/10 Denatured Alcohol (SD 3C, 190 Proof)/water was used instead of the alcohol alone.

2.B SR-coated Fumaric Acid-Containing Cores: The fumaric acid cores (3750 g) from above were coated with a solution of EC-10 and either PEG 400 (B.1) at a ratio of 60/40 or TEC (B.2) at a ratio of 90/10 as the plasticizer, dissolved in 98/2 acetone/water (6% solids) for a weight gain of 10%.

2.C Ondansetron Hydrochloride IR Beads: Ondansetron hydrochloride IR beads from B.1 and B.2 above were prepared as disclosed in Example 1.C. The drug-layered beads were provided with a protective seal-coat with Pharmacoat® 603 (hypromellose 2910; 3 cps) for a weight gain of 2%.

2.D Ondansetron Hydrochloride SR Beads: Ondansetron hydrochloride IR beads (1080 g) were barrier-coated (SR coated) by spraying a solution of EC-10 and either PEG 400 (D.1) at a ratio of 60/40 or TEC (D.2) at a ratio of 90/10 as the plasticizer, dissolved in 98/2 acetone/water (7.5% solids) for a weight gain of 10% and dried in the Glatt at the same temperature for 10 minutes to drive off excess residual solvent. The dried beads were sieved to discard any doubles if formed.

Figure 3:
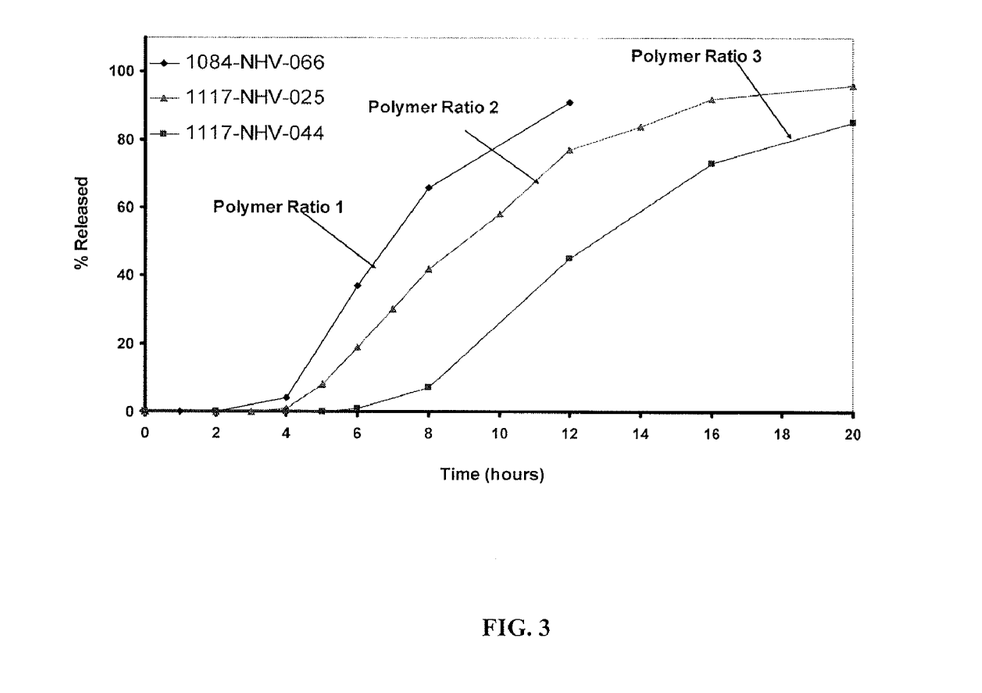
FIG. 3 illustrates the release profiles of ondansetron hydrochloride from the TPR particles of Example 2.

2.E Ondansetron Hydrochloride TPR Beads: Ondansetron hydrochloride SR beads from D.1 and D.2 above were further coated with a lag-time coating membrane of EC-10/HP-55/TEC at three ratios of 45.5/40/14.5 (E.1—Lot#1084-066), 50.5/35/14.5 (E.2—Lot#1117-025) and 60.5/25/14.5 (E.3—Lot#1117-044) dissolved in 90/10 acetone/water (7.5% solids) for a gain of up to 50% by weight. The TPR beads were dried in the Glatt to drive off residual solvent and sieved through an 18 mesh sieve. FIG. 3 shows the release profiles for ondansetron hydrochloride from TPR beads coated with EC-10/HP-55/TEC at three different ratios (E.1, E.2 and E.3). More specifically, FIG. 3 shows the release profiles for the following formulations:

(1) TPR beads Lot#1084-066—The coating of EC-10/HP-55/TEC at a ratio of 45.5/40/14.5 at 50% by weight applied on IR beads coated with 60/40 EC-10/PEG 400 (7.5% solids) at 10% while IR beads (5% drug layered from 90/10 ondansetron/PVP) comprise fumaric acid cores (4% layered on sugar spheres from acid/Klucel) coated with 60/40 EC-10/PEG 400 at 10%.

(2) TPR beads Lot#1117-025—The coating of EC-10/HP-55/TEC at a ratio of 50.5/35/14.5 (7.5% solids) at 50% by weight applied on IR beads coated with 90/10 EC-10/TEC (7.5% solids) at 10% while IR beads (6% drug layered from 90/10 ondansetron/Klucel LF at 5% solids) comprise fumaric acid cores (layered on sugar spheres from acid/PVP) coated with 90/10 EC-10/TEC at 7.5% solids for a drug load of 10% by weight.

(3) TPR beads Lot#1117-044—The coating of EC-10/HP-55/TEC at a ratio of 60.5/25/14.5 at 50% by weight applied on IR heads coated with 90/10 EC-10/TEC at 10% while IR beads (6% drug layered from 90/10 ondansetron/Klucel LF) comprise fumaric acid cores (layered on sugar spheres from acid/PVP) coated with 90/10 EC-10/TEC at 10%.

EXAMPLE 3

3.A Fumaric Acid-Containing Cores: Hydroxypropyl cellulose (Klucel LF, 53.6 g) was slowly added to 90/10 190 proof alcohol/water at 4% solids while stirring rigorously until dissolved and then fumaric acid (482.1 g) was slowly added until dissolved. A Glatt GPCG 5 equipped with a 9" bottom spray Wurster insert, 10" partition column was charged with 3750 g of 25-30 mesh sugar spheres. The sugar spheres were layered with the fumaric acid solution while maintaining the product temperature at about 33-35° C. and a spray rate of 8-60 mL/min. The acid cores were dried in the unit for 10 min to drive off residual solvent/moisture and sieved through 40-80 mesh.

3.B SR-coated Fumaric Acid-Containing Cores: The acid cores (3750 g) from above were coated with a solution (at 7.5% solids) of 177.6 g of ethylcellulose (EC-10) and 19.7 g of triethyl citrate (TEC) at a ratio of 90/10 dissolved in 95/5 acetone/water for a weight gain of 5% by weight following the procedures disclosed above.

3.C Ondansetron Hydrochloride IR Beads: Hydroxypropyl cellulose (Klucel LF, 44.3 g) was slowly added to 50/50 190 proof alcohol/water (4247.4 g alcohol+4247.4 g water at 5% solids) while stirring rigorously to dissolve and ondansetron HCl (402.8 g) was slowly added while stirring to dissolve the drug. SR coated acid cores (3500 g) were coated in the Glatt GPCG 5 with the drug solution, and the drug-layered beads were provided with a protective seal-coat of Pharmacoat 603 (80.5 g for about 2% weight gain) and dried in the Glatt to produce IR beads (batch size: 4028 g).

3.D Ondansetron Hydrochloride SR Beads: Ondansetron Hydrochloride IR beads (3500 g) were barrier-coated (SR coated) by spraying a solution (7.5% solids) of 90/10 EC-10/TEC at 5% by weight and dried in the Glatt at the same temperature for 10 minutes to drive off excess residual solvent. The dried beads were sieved to discard any doubles if formed.

3.E Ondansetron Hydrochloride TPR Beads: Ondansetron hydrochloride SR beads (2600 g) from above were further coated with a lag-time coating membrane of EC-10/HP-55/TEC at a ratio of 60.5/25/14.5 dissolved in 90/10 acetone/water (7.5% solids) for a weight gain of 30%, 45%, and 50%. The coated beads were cured at 60° C. for 30 minutes in the same unit and sieved through a 18 mesh sieve after cooling to ambient temperature.

Figure 4:
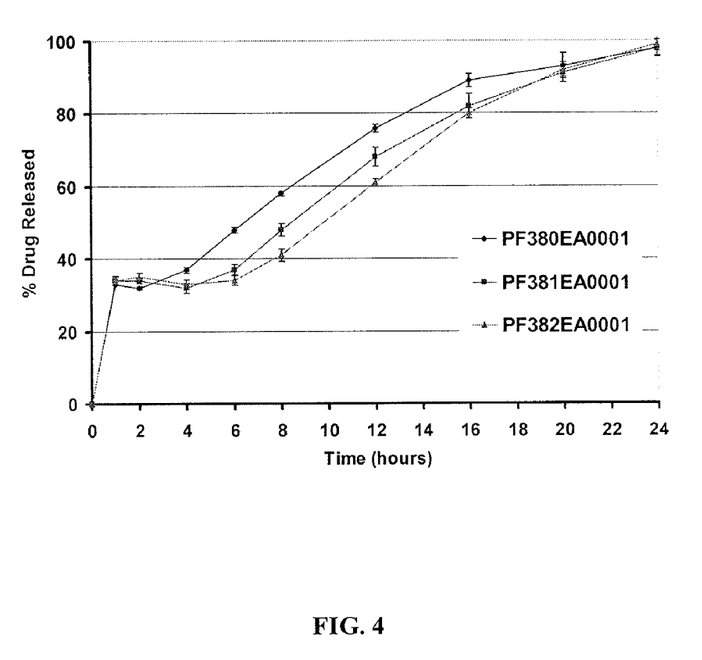
FIG. 4 illustrates the release profiles from MR capsules comprising IR and TPR beads at a ratio of 35/65 by weight of Example 3.
Figure 5:
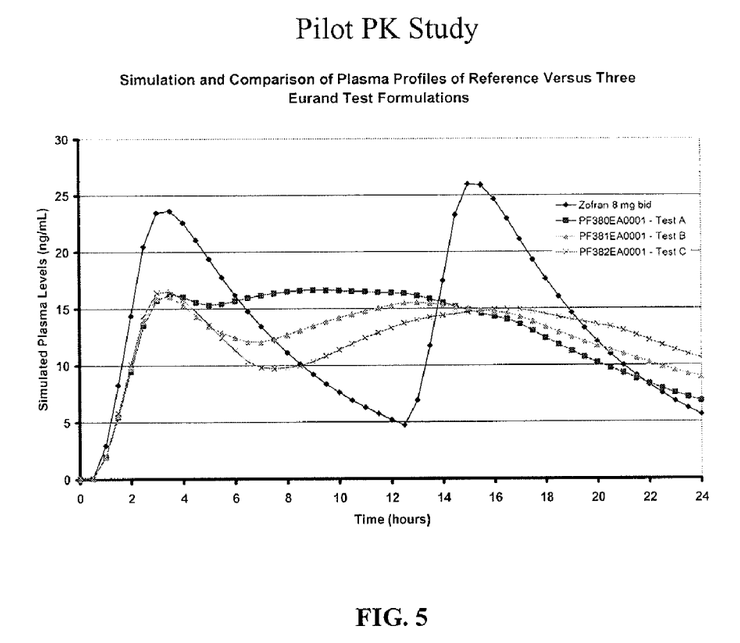
FIG. 5 compares the simulated ondansetron plasma profiles of MR capsules of Example 3 with the actual plasma profiles observed in the pilot PK study of Example 4.

3.F Ondansetron Hydrochloride MR Capsules: Ondansetron hydrochloride IR beads (PE364EA0001) and TPR beads (Lot# PE366EA0001 with a lag-time coating of 30%, Lot# PE367EA0001 with a lag-time coating of 45%, and Lot# PE368EA0001 with a lag-time coating of 50%) were encapsulated at a ratio of 35%/65% into hard gelatin capsules to produce MR (modified-release) Capsules, 16 mg (lots# PF380EA0001, lots# PF381EA0001, and lots# PF382EA0001) QD (dosed once-daily) for a pilot bioavailability study in humans in comparison to marketed Zofran® 8 mg (as ondansetron) dosed bid (two times a day). FIG. 4 shows the drug-release profiles from the three MR Capsules comprising IR and TPR beads. Using the in vitro drug release profiles presented in FIG. 4, the calculated ondansetron plasma concentration—time profiles are presented in FIG. 5.

EXAMPLE 4

A 4-arm crossover pilot POC (proof of concept) study was conducted which included 12 Caucasian male, healthy volunteers aged 18 to 55 years with a wash-out period of 7 days. Each volunteer was dosed with 250 mL of mineral water a single dose of 16 mg Test Formulation (either A (PF380EA0001), B (PF381EA0001), or C (PF382EA0001) of Example 3) at 8 am or two 8 mg Zofran® (i.e., one at 8 am and the other at 4:30 pm after an overnight fasting (at least 12 hrs), and lunch was served at 11 am. Blood samples were drawn at 0 (pre-dose), 20 min, 40 min, 1 hr, 1.5 hrs, 2 hrs, 3 hrs, 4 hrs, 6 hrs, 8.5 hrs (before second dose), 9 hrs 10 min, 9.5 hrs, 10 hrs, 10.5 hrs, 11.5 hrs, 12.5 hrs, 14.5 hrs, 17 hrs, 20 hrs, 22 hrs, 24 hrs and 36 hrs. The PK (pharmacokinetics) profiles are presented in FIG. 6. The pilot PK study demonstrate that the plasma profiles of Test Formulations A (PE380EA0001), B (PE381EA0001), and C (PE382EA0001) are those characteristic of sustained release formulations, i.e., apparent half-life is significantly longer than that with Zofran®. AUC or $C_{max}$ of Test Formulations does not deviate substantially from that of Zofran® (i.e., AUC within ±25% and $C_{max}$ approximately 70% of Zofran®). The actual $C_{max}$ for Zofran® 8 mg was 30 ng/mL in comparison to the predicted 24 ng/mL while the actual $C_{max}$ for the IR component was about 24 ng/mL when normalized. Approximately 70% of Zofran® 8 mg bid (twice-dosed) was absorbed in 24 hrs. Test Formulations A to C exhibited the expected trend post-dosing up to the crossover point at about 15-16 hrs; thereafter, Formula C continued to exhibit a lower plasma concentration-time profile contrary to the predicted behavior.

Figure 6:
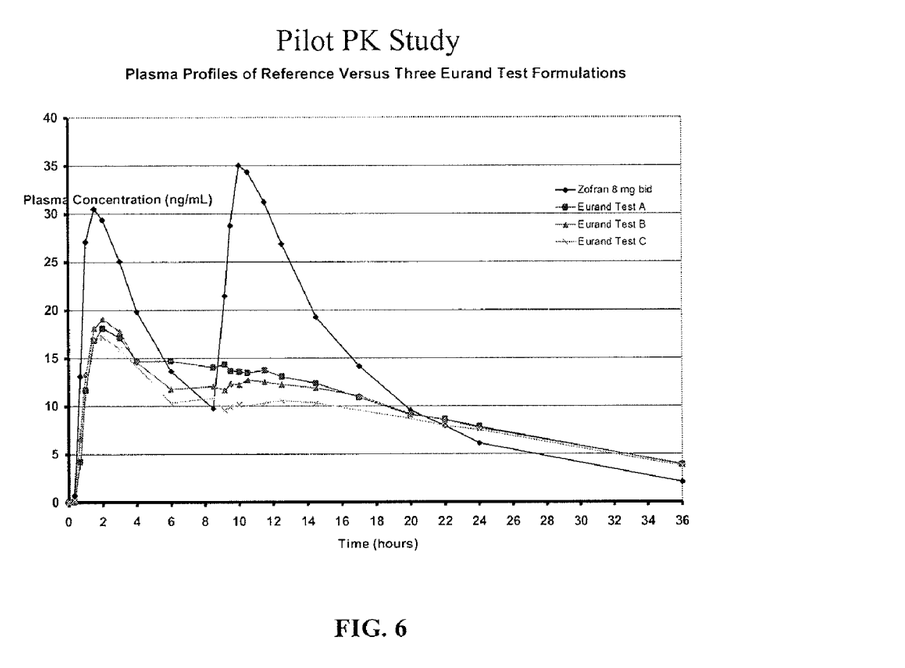
FIG. 6 compares the actual plasma profiles observed in the pilot PK study of Example 4.

It is apparent from FIG. 6 that the incorporation of an organic acid, as the solubilizer for the weakly basic drugs exhibiting a pH-dependent solubility profile (i.e., showing a decrease in solubility at the intestinal pH 6.8 by about 2 orders of magnitude in comparison to its maximum solubility in the GI fluid) and functional coating of the acid before applying the active ingredient has significant impact on the lag time, a desired but complete drug release profile prior to depletion of the buffer and hence complete absorption in the distal part of the GI tract where the drug is practically insoluble.

Figure 7:
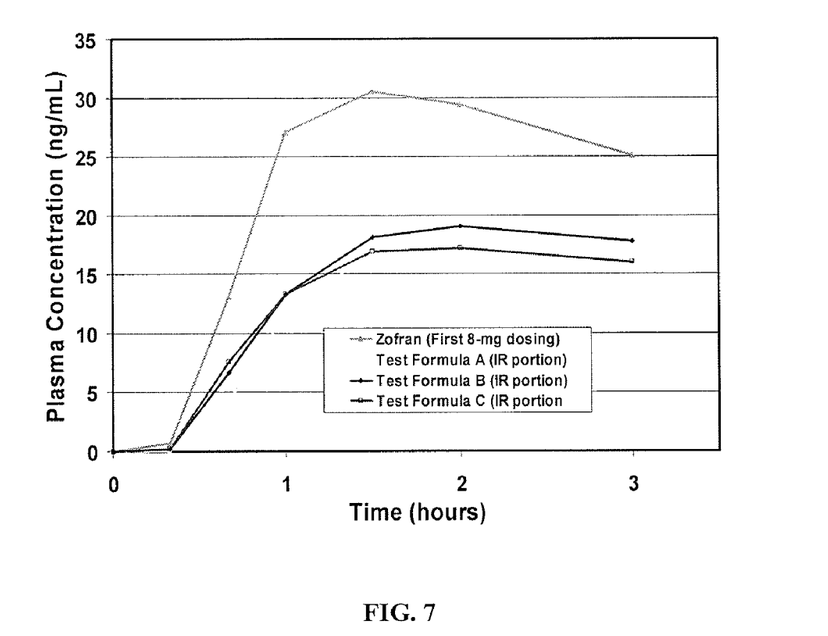
FIG. 7 illustrates the ondansetron plasma profiles corresponding to the IR portions of MR capsules versus Zofran® first dose observed in the pilot PK study of Example 4.

It is apparent from FIG. 7 that the release and hence absorption of the immediate release portion of the test dosage forms are significantly slower and incomplete in comparison to that of a single dose of the reference product, Zofran.

Figure 8:
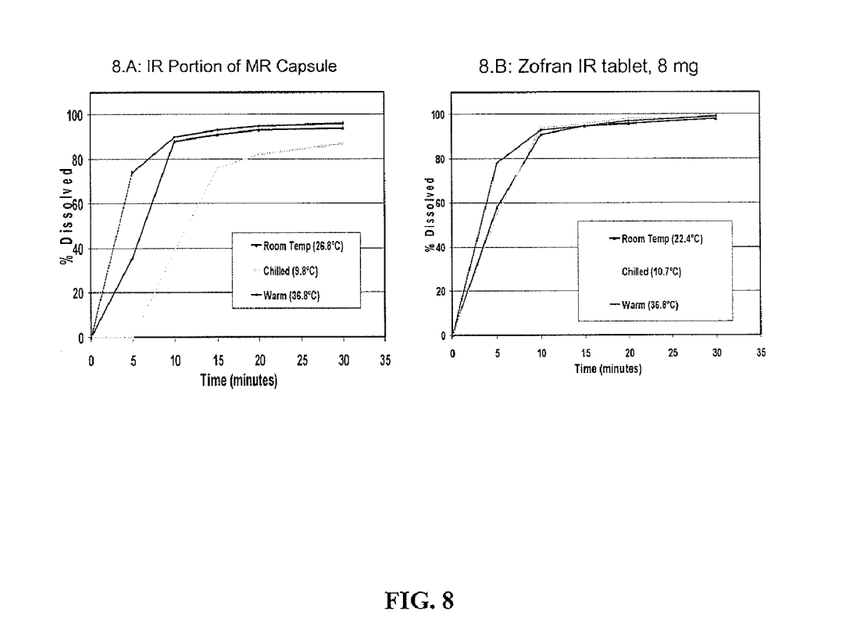
FIG. 8 illustrates the in vitro release profiles of the IR portions of MR capsule (PF EA0001) of Example 4 versus Zofran® when dissolution tested in 0.1N HCl at different temperatures.

Investigations were carried out to develop a discriminatory dissolution methodology in an attempt to understand differences in performance between the test and reference formulations and to reformulate the IR portion of the test formulation with a dissolution profile similar to that of the test product. FIG. 8 shows the dissolution profiles of the IR beads that were incorporated into the test capsule formulations versus Zofran® when dissolution tested at different temperatures. Although the dissolutions from IR beads in 0.1N HCl were slower at lower temperatures, temperature alone did not appear to account for the observed differences. The drug's solubility decreases by about 2 orders of magnitude upon the change in pH from 1.2 to pH 6.8, it was hypothesized a delay in gastric emptying for example would cause a delay in $C_{max}$.

EXAMPLE 5

5.A Ondansetron Hydrochloride RR Beads at a drug load of 5%: Hydroxypropylcellulose (Klucel LF from Aqualon, 16.5 g) was slowly added to 50/50 water/Denatured Alcohol 3C, 190 Proof (1500 g each) while mixing to dissolve. Ondansetron hydrochloride dihydrate (150 g) was slowly added to the binder solution to dissolve the drug. 60-80 mesh sugar spheres (2773.5 g) were coated in the Glatt GPCG 5 with the drug solution (5% solids) to achieve a drug load of 5% by weight under the following conditions (air distribution plate: B with 100 mesh screen; nozzle diameter: 1 mm; partition height: 10"; 9" bottom spray Wurster insert; product temperature at 36-37° C.; inlet air volume at 60-65 cfm and spray rate being increased from about 20-25 g/min). The drug-layered beads were provided with a protective seal-coat of Pharmacoat 603 (hypromellose 2910; 3 cps) (2% weight gain) to form RR beads. The RR beads were dried in the unit for 10 min to drive off residual solvent/moisture and sieved through 40-80 mesh screens. More than 90% of the IR beads were in the particle size range of <50-100> mesh.

5.B Ondansetron Hydrochloride RR Beads at a drug load of 10%: Hydroxypropylcellulose (33.0 g) was slowly added to 50/50 water/Denatured Alcohol 3C, 190 Proof (2500 g each) while mixing to dissolve. Ondansetron hydrochloride (300 g) was slowly added to the binder solution to dissolve the drug. 60-80 mesh sugar spheres (2607 g) were coated in the Glatt GPCG 5 with the drug solution (5% solids) to achieve a drug load of 10% by weight under the above conditions. More than 90% of the RR beads were in the particle size range of <50-100> mesh.

5.C Ondansetron Hydrochloride RR Granules at a drug load of 10%: Fumaric acid (270 g) followed by Klucel LF (120 g) and ondansetron HCl (600 g) was slowly added to a 50/50 mixture of Denatured 190 Proof Ethyl Alcohol and water (5000 g each) in a stainless steel tank to dissolve while agitating. A Glatt GPCG 5 equipped with a top spray Wurster insert was pre-heated for not less than 30 min and charged with spray dried lactose (Fast Flo Lactose; 2130 g), microcrystalline cellulose (MCC, Avicel PH102; 2400 g); Crospovidone (XL-10; 480 g) and granulated while spraying 25-100 g/min under the following conditions: granulating bowl: GPCG 5 with top spray; nozzle tip: 1.2 mm; inlet air temperature: 55° C.; Air flow target: 80 cfm; Atomization air pressure: 2.0 bar; product temperature target: 50° C. The granulation was dried at 55° C. for a loss on drying value of <2%. The granules were sieved through a 20 mesh and blended with magnesium stearate (10 g per 5000 g of granules) in a 0.5 cu.ft. V blender rotating at 21 rpm for 5 minutes.

Figure 9:
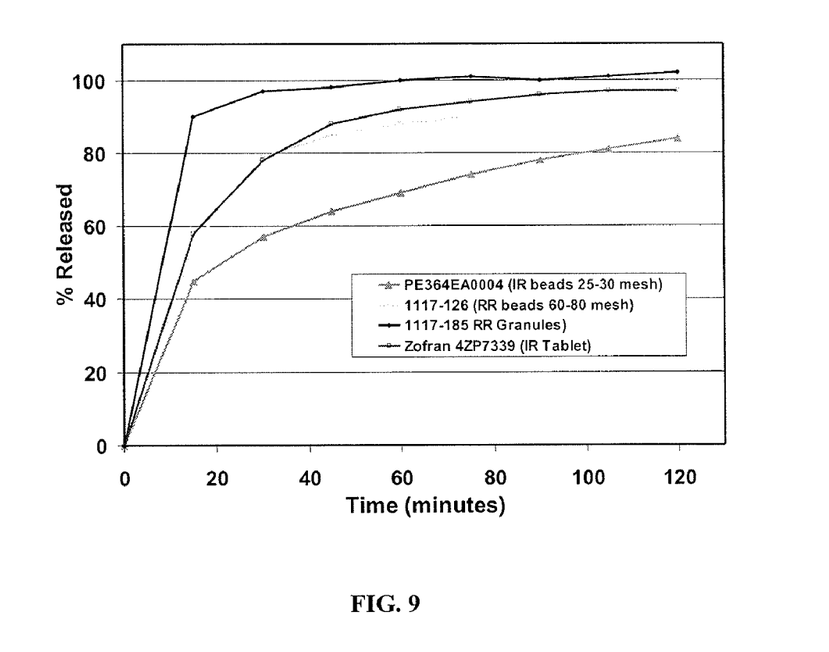
FIG. 9 illustrates the in vitro release profiles of Zofran® versus IR beads (PE364EA0004), of Example 3, RR (rapid release) drug particles (drug layered beads, Lot #1117-126 of Example 5.B) or granules (Lot#1117-185, of Example 5.C) when dissolution tested at pH 6.8.

Dissolution profiles of the rapid release drug particles (drug-layered onto 60-80 mesh sugar spheres and water-soluble lactose and fumaric acid containing granules) of Examples 5.A, 5.B and 5.C are shown to be similar to that of Zofran® 8 mg IR tablets when dissolution tested at pH 6.8 (see FIG. 9 showing the dissolution profiles for IR beads layered on 25-30 mesh sugar spheres of Ex. 3.0 (Lot# PE364EA0004 used to fill into MR capsules used in the POC study of Ex. 4), RR beads of Ex. 5.B (Lot#1117-126), RR granules of Ex. 5.0 (Lot#1117-185) and for Zofran).

EXAMPLE 6

6.A Fumaric Acid-Containing Cores: 25-30 mesh sugar spheres (3750 g) were layered with fumaric acid (482.1 g) from a solution (4% solids) of Klucel LF (53.6 g) as disclosed in Example 3 to achieve an acid load of 11.25% by weight. The acid cores were dried in the unit for 10 min to drive off residual solvent/moisture and sieved through 20-30 mesh screens.

6.B SR-coated Fumaric acid Cores: The acid cores (3750 g) from above were coated with a solution of 177.6 g of ethylcellulose (EC-10) and 19.7 g of triethyl citrate (TEC) at a ratio of 90/10 dissolved in 95/5 acetone/water (7.5% solids) for a weight gain of 5%.

6.C Ondansetron Hydrochloride IR Beads: IR beads of ondansetron hydrochloride dihydrate with a drug load of 10% by weight were produced by spraying a solution (5% solids) of ondansetron hydrochloride dihydrate (402.8 g) and Klucel LF (44.3 g) in a 50/50 ethanol/water mixture (4247.4 g each) onto fumaric acid SR beads (3500 g) in a Glatt GPCG 5 under the following conditions: Air distribution plate: B with 15 gauge 100 mesh screen; Nozzle diameter: 1 mm; Partition height: 10"; 9" bottom spray Wurster insert; Product temperature at 34±1° C.; Inlet air volume at 150 cfm; Atomization air pressure—1.5 bar; and Spray rate being increased from 8 to 30 mL/min. The drug-layered beads were provided with a protective seal-coat of Pharmacoat 603 (hypromellose 2910; 3 cps) (2% weight gain) to form IR beads. The IR beads were dried in the unit for 10 min to drive off residual solvent/moisture and sieved to discard oversized and undersized particles.

6.D Ondansetron Hydrochloride TPR Beads at 15% Coating: Ondansetron hydrochloride IR beads (3500 g) were applied with a lag time coating (ratio: 63:22:15) of ethylcellulose (389.1 g), HP-55 (hypromellose phthalate, 135.9 g) and TEC (triethyl citrate, 92.6 g) in 90/10 acetone/water by spraying the solution (18% solids) at 15% by weight and dried in the Glatt at the same temperature for 10 minutes to drive off excess residual solvent. The dried beads are sieved to discard any doubles if formed.

6.E Ondansetron Hydrochloride TPR Beads at 10% Coating: Ondansetron hydrochloride IR beads (3500 g) were applied with a lag time coating (ratio: 63:22:15) of ethylcellulose (245.0 g), HP-55 (hypromellose phthalate, 85.6 g) and TEC (triethyl citrate, 58.3 g) in 90/10 acetone/water by spraying the solution (18% solids) at 10% by weight and dried in the Glatt at the same temperature for 10 minutes to drive off excess residual solvent. The dried beads were sieved to discard any doubles if formed.

EXAMPLE 7

7.A Ondansetron Hydrochloride MR Capsules PF391E0001: Appropriate amounts of Rapid Release Granules (100.0 mg of RR granules of Lot# PE391EA0001) prepared as disclosed in 5.0 and TPR beads (166.2 mg of TPR beads of Lot# PE392EA0001) prepared as disclosed in 6.E were filled into size '0' hard gelatin capsules to produce Test Formulations A: MR Capsules, 20 mg (8 mg RR+12 mg TPR ($T_{80\%}$~8 hrs)).

7.B Ondansetron Hydrochloride MR Capsules PF392EA0001: Appropriate amounts of Rapid Release Granules (100.0 mg of RR granules of Lot# PE391EA0001) prepared as disclosed in 5.0 and TPR beads (221.6 mg of TPR beads of Lot# PE292EA0001) prepared as disclosed in 6.E were filled into size '0' hard gelatin capsules to produce Test Formulations B: MR Capsules, 24 mg (8 mg RR+16 mg TPR ($T_{80\%}$~8 hrs)).

7.C Ondansetron Hydrochloride MR Capsules PF379EA0001: Appropriate amounts of Rapid Release Granules (100.0 mg of RR granules of Lot# PE391EA0001) prepared as disclosed in 5.0 and TPR beads (234.6 mg of TPR beads of Lot# PE393EA0001) prepared as disclosed in 6.D were filled into size '0' hard gelatin capsules to produce Test Formulations C: MR Capsules, 24 mg (8 mg RR+16 mg TPR ($T_{80\%}$~12 hrs)).

Figure 10:
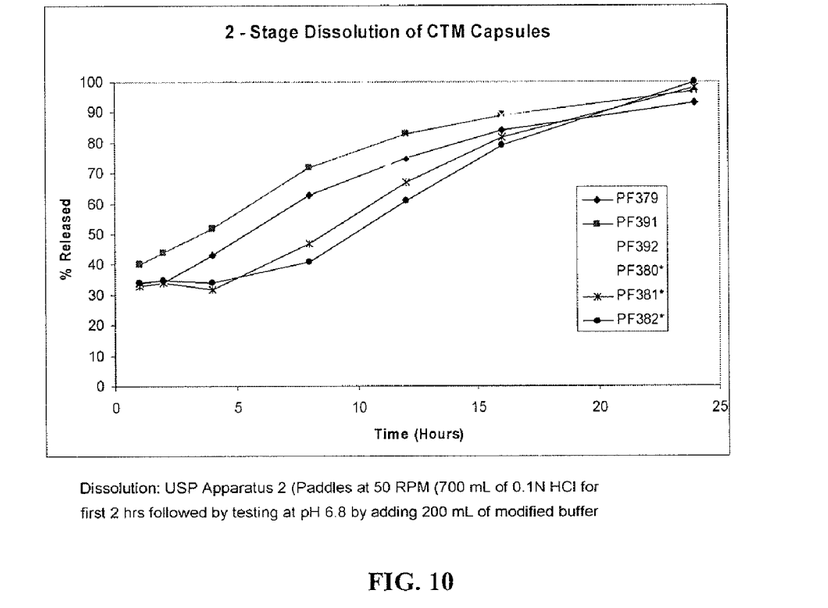
FIG. 10 illustrates the drug release profiles from MR capsule formulations of Example 3 (PF380EA0001, PF381EA0001, and PF382EA0001) versus MR capsule formulations of Example 6 (PF391EA0001, PF392EA0001, and PF379EA0001).

FIG. 10 demonstrates the release profiles from the MR capsule formulations used in the POC study of Example 4, which were coated with a barrier coating and a lag-time coating with EC-10/HP-55/TEC at a ratio of 60.5/25/14.5 for a weight gain of 30%, 45%, and 50% (PF380EA0001, PF381EA0001, and PF382EA0001, all containing 8 mg IR beads+8 mg TPR beads)) and MR capsule formulations, PF391EA0001 (8 mg RR granules+12 mg TPR beads), PF392EA0001 (8 mg RR granules+16 mg of TPR beads), and PF379EA0001 (8 mg RR granules+16 mg of TPR beads). All MR capsule formulations were dose adjusted (IR/RR component to 8 mg and TPR component to 12-mg or 16-mg). The MR capsule formulations of Example 7 (PF391EA0001, PF392EA0001, and PF379EA0001) have shorter lag times as well as faster release profiles in order to maximize ondansetron release and concomitant absorption in the distal part of the GI tract.

Figure 11:
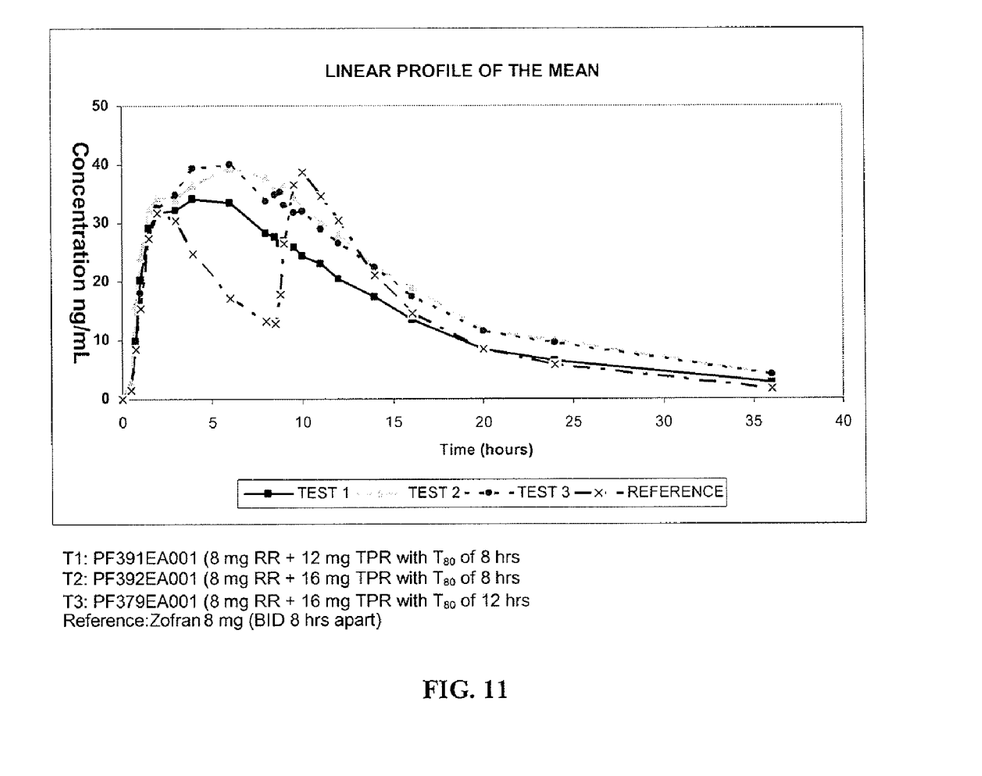
FIG. 11 illustrates the ondansetron plasma concentration—time profiles of MR capsule formulations (PF391EA0001, PF392EA0001, and PF379EA0001) comprising RR Granules (rapid release granules) and TPR beads of Example 7.

7.D Pilot PK Study on Ondansetron Hydrochloride MR Capsules vs. Zofran: A 4-arm crossover pilot PK (pharmacokinetics) study was conducted which included 12 Caucasian male, healthy volunteers aged 18 to 55 years with a wash-out period of 7 days. Each volunteer was dosed with 250 mL of still mineral water, a single Test 1 (20 mg; PF391EA0001), Test 2 (24 mg; PF391EA0001), or Test 3 (24 mg; PF379EA0001) of Example 7, at 8 a.m., or two Zofran® (8 mg) at 8 a.m. and 4:30 p.m. after an overnight fasting (at least 12 hrs and lunch was served at 11 a.m.). Blood samples were drawn at 0 (pre-dose), 20 min, 40 min, 1 hr, 1.5 hrs, 2 hrs, 3 hrs, 4 hrs, 6 hrs, 8.5 hrs (before second dose), 9 hrs 10 min, 9.5 hrs, 10 hrs, 10.5 s, 11.5 hrs, 12.5 hrs, 14.5 hrs, 17 hrs, 20 hrs, 22 hrs, 24 hrs and 36 hrs. FIG. 11 demonstrates the mean plasma concentration-time profiles achieved. The ratios of the PK parameters (the actual as well as the dose normalized) are presented in Table 2. The relative bioavailability compared to 8 mg IR bid reference was approximately 0.85 for all test formulations (Test Formula A, B, and C) at the end of 24 hours.

TABLE 2

PK Parameters from Pilot PK Study

| PK Parameters Mean (90% C.I.) | Test-A (Ondansetron 20 mg PF391EA0001) | Test-B (Ondansetron 24 mg PF392EA0001) | Test-C (Ondansetron 24 mg PF379EA0001) |
|---|---|---|---|
| $C_{max}$ | 89% (84-95%) | 107% (100-114%) | 104% (97-111%) |
| $AUC_t$ | 109% (102-117%) | 132% (132-152%) | 137% (128-146%) |
| $AUC_{inf}$ | 113% (105-122%) | 150% (139-161%) | 145% (135-146%) |
| Dose Normalized PK Parameters | | | |
| Relative Bioavailability (90% Confidence Interval) | 92% (86-98%) | 98% (92-104%) | 95% (89-101%) |

EXAMPLE 8

8.A Fumaric Acid-Containing Cores: Microcrystalline cellulose spheres (Cellets 100 with a mean particle size of about 100 μm from Glatt; 933.3 g) are layered with fumaric acid (240 g) from a solution (4% solids) of Klucel LF (26.7 g) as disclosed in Example 3 to achieve an acid load of 10% by weight. The acid cores are dried in the unit for 10 min to drive off residual solvent/moisture and sieved through 40-150 mesh screens.

8.B Fumaric Acid SR Beads: The acid cores (900 g) from above are coated with a solution of 270 g of ethylcellulose (EC-10) and 30 g of triethyl citrate (TEC) at a ratio of 90/10 dissolved in 95/5 acetone/water (7.5% solids) for a weight gain of 25%.

8.C Ondansetron IR Beads at a drug load of 13%: IR beads of ondansetron hydrochloride dihydrate with a drug load of 13% by weight are produced by spraying a solution of ondansetron hydrochloride dihydrate (140.4 g) and Klucel LF (15.6 g) in a 50/50 ethanol/water mixture (1560 g each) onto SR coated acid beads (900 g) in a Glatt GPCG 3. The drug-layered beads are provided with a protective seal-coat of Pharmacoat® 603 (hypromellose 2910; 3 cps) (2% weight gain) to form IR beads. The IR beads are dried in the unit for 10 min to drive off residual solvent/moisture and sieved to discard oversized and undersized particles.

8.D Ondansetron TPR Beads: Ondansetron hydrochloride IR beads are applied with a lag time coating of EC-10/HP-55/TEC (ratio: 68:22:10) in 90/10 acetone/water by spraying the solution (7.5% solids) for a weight gain of 30%, 35%, and 40%, and dried in the Glatt at the same temperature for 10 minutes to drive off excess residual solvent. The dried beads are sieved to discard any doubles if formed 8.E Taste Masked IR Beads: Ondansetron IR beads prepared in accordance with the disclosures of Example 8.0 are taste-masked by coating in a fluid bed coater (e.g., a Glatt GPCG 3) with a solution of Ethocel 10 cps and Eudragit® EPO at a ratio of 50:50 in accordance with the disclosures of co-pending patent application Ser. No. 11/248,596 filed Oct. 12, 2005 for a weight gain of 20%. The taste masked beads are dried in the unit for 10 min to drive off residual solvent/ moisture and sieved through 40-80 mesh screens.

8.F Rapidly-dispersible microgranules: The rapidly-dispersing microgranules comprising a sugar alcohol such as mannitol and a disintegrant such as crospovidone are prepared following the procedure disclosed in the co-pending US Patent Application Publication No. U.S. 2005/0232988, published Oct. 20, 2005, the contents of which are hereby incorporated by reference. D-mannitol (152 kg) with an average particle size of approximately 20 μm or less (Pearlitol 25 from Roquette, France) is blended with 8 kg of cross-linked povidone (Crospovidone XL-10 from ISP) in a high shear granulator (GMX 600 from Vector) and granulated with purified water (approximately 32 kg) and wet-milled using a rotary mill from Quadro and dried in a Greunburg oven. The rapidly-dispersing microgranules thus obtained will have an average particle size in the range of approximately 20-300 μm.

8.G Ondansetron Hydrochloride ODT MR, 24 mg: Rapidly-dispersing microgranules (5600 g) are blended with taste masked IR beads (769 g), TPR beads at 40% coating (2051 g), and pre-blended excipient mixture of a flavor, a sweetener, and additional disintegrant (1580 g), in a twin shell V-blender for 15 minutes to get homogeneously distributed blend for compression. Tablets weighing approximately 1000 mg are compressed using a production scale tablet press equipped with an external lubrication system at a mean hardness in the range of about 40-50 N and friability of about <0.5% by weight. Ondansetron Hydrochloride Dihydrate MR ODT, 24 mg thus produced rapidly disintegrates in the oral cavity creating a smooth, easy-to-swallow suspension comprising coated ondansetron hydrochloride beads, which will provide a target profile suitable for a once-daily dosing regimen.

From these demonstrations, it is apparent that the incorporation of an organic acid, as the solubilizer in TPR beads comprising a weakly basic selective serotonin 5-HT$_3$ blocking agent exhibiting a pH-dependent solubility profile (i.e., showing a decrease in solubility at the intestinal pH 6.8 by about 2 orders of magnitude in comparison to its maximum solubility in the gastric fluid) and functional coating of the acid before applying the active pharmaceutical ingredient has significant impact on the lag time, a desired but complete drug release profile prior to depletion of the buffer. Furthermore, the active pharmaceutical ingredient remains in the unaltered form in the solid dosage form until it is released for absorption in the GI tract. Furthermore, the bolus dose comprising rapid release drug particles is designed to provide a faster dissolution similar to that of the reference drug product.

We claim:

1. A pharmaceutical composition comprising a plurality of timed pulsatile release and rapid release particles, wherein:
   the timed pulsatile release particles each comprise a core coated with a timed pulsatile release layer;
   the core comprises a weakly basic, poorly soluble drug and a pharmaceutically acceptable organic acid wherein the weakly basic drug is disposed over the organic acid and wherein a sustained release layer comprising a water insoluble polymer optionally in combination with a water soluble polymer or an enteric polymer, is disposed between the weakly basic drug and the organic acid;
   the rapid release particles each comprise the weakly basic, poorly soluble drug, and release at least about 80 wt. % of the weakly basic, poorly soluble drug in about 15 minutes when dissolution tested using United States Pharmacopoeia (USP) dissolution methodology (Apparatus 2—paddles@50 RPM and a two-stage dissolution medium at 37° C. (first 2 hours in 0.1N HCl followed by testing in a buffer at pH 6.8).

2. The pharmaceutical composition of claim 1, wherein the core comprises a first inert bead, an organic acid layer, the sustained release layer, and a drug layer;
   wherein:
      the organic acid layer comprises the pharmaceutically acceptable organic acid and a first pharmaceutically acceptable polymeric binder;
      the sustained release layer comprises a first pharmaceutically acceptable water insoluble polymer; and
      the drug layer comprises the weakly basic, poorly soluble drug and a second pharmaceutically acceptable polymeric binder.

3. The pharmaceutical composition of claim 1, wherein the timed pulsatile release layer comprises a pharmaceutically acceptable water insoluble polymer and an enteric polymer.

4. The pharmaceutical composition of claim 1, wherein the rapid release particles each comprise an inert bead and a drug layer comprising the weakly basic, poorly soluble drug and a pharmaceutically acceptable polymeric binder; or the rapid release particles each comprise a granulate comprising the weakly basic, poorly soluble drug, a pharmaceutically acceptable polymeric binder, at least one excipient, and at least one disintegrant.

5. The pharmaceutical composition of claim 2, wherein the rapid release particles each comprise a second inert bead and a drug layer comprising the weakly basic, poorly soluble drug and a pharmaceutically acceptable polymeric binder.

6. The pharmaceutical composition of claim 2, wherein the rapid release particles each comprise a granulate comprising the weakly basic, poorly soluble drug, a pharmaceutically acceptable organic acid, a pharmaceutically acceptable polymeric binder, and at least one excipient.

7. The pharmaceutical composition of claim 2, wherein the pharmaceutically acceptable organic acid is selected from the group consisting of citric acid, lactic acid, fumaric acid, malic acid, maleic acid, tartaric acid, succinic acid, oxalic acid, aspartic acid, and glutamic acid.

8. The pharmaceutical composition of claim 2, wherein the first and second pharmaceutically acceptable polymeric binders are each independently selected from the group consisting of polyvinylpyrrolidone, copolymers of polyvinylpyrrolidone and vinyl alcohol, copolymers of polyvinylpyrrolidone and vinyl acetate, copolymers of polyvinylpyrrolidone with vinyl chloride, copolymers of polyvinylpyrrolidone with vinyl butyrate, copolymers of polyvinylpyrrolidone with vinyl laurate, copolymers of polyvinylpyrrolidone with vinyl stearate, hydroxypropylcellulose, hydroxypropylmethyl cellulose, carboxyalkylcelluloses, polyethylene oxide, sodium carboxymethyl cellulose, dextran, acacia, starch, and gelatin.

9. The pharmaceutical composition of claim 1, wherein the weakly basic, poorly soluble drug comprises a serotonin 5-$HT_3$ receptor antagonist.

10. The pharmaceutical composition of claim 9, wherein the serotonin 5-$HT_3$ receptor antagonist is selected from the group consisting of ondansetron, tropisetron, granisetron, dolasetron, and palonosetron.

11. The pharmaceutical composition of claim 2, wherein the weakly basic, poorly soluble drug comprises a serotonin 5-$HT_3$ receptor antagonist.

12. The pharmaceutical composition of claim 11, wherein the serotonin 5-$HT_3$ receptor antagonist is selected from the group consisting of ondansetron, tropisetron, granisetron, dolasetron, and palonosetron.

13. The pharmaceutical composition of claim 2, wherein the pharmaceutically acceptable water insoluble polymer selected from the group consisting of ethyl cellulose, cellulose acetate, polyvinyl acetate, neutral copolymers of ethyl acrylate and methylmethacrylate, copolymers of acrylic and methacrylic esters containing quaternary ammonium groups, and waxes.

14. The pharmaceutical composition of claim 3, wherein the enteric polymer is selected from the group consisting of cellulose acetate phthalate, hydroxypropyl methylcellulose phthalate, hydroxypropyl methylcellulose acetate succinate, polyvinyl acetate phthalate, pH-sensitive copolymers of methacrylic acid and methylmethacrylate, and shellac.

15. The pharmaceutical composition of claim 5, wherein the first inert bead has an average particle size of about 25-30 mesh, and the second inert bead has an average particle size selected from the group consisting of about 45-60 mesh, about 60-80 mesh, and about 80-200 mesh.

16. The pharmaceutical composition of claim 15, wherein the first and second inert beads comprise sugar or microcrystalline cellulose.

17. The pharmaceutical composition of claim 6, wherein the timed pulsatile release particles each comprise a 25-30 mesh sugar bead sequentially coated with the organic acid layer, a first sustained release layer; the drug layer; an optional sealing layer; and an optional second sustained release layer.

18. The pharmaceutical composition of claim 17, wherein the organic acid layer comprises fumaric acid and hydroxypropyl cellulose.

19. The pharmaceutical composition of claim 17, wherein the first sustained release layer comprises ethylcellulose and a pharmaceutically acceptable plasticizer.

20. The pharmaceutical composition of claim 17, wherein the second sustained release layer is present and comprises ethylcellulose and a pharmaceutically acceptable plasticizer.

21. The pharmaceutical composition of claim 20, wherein the first and second sustained release layers comprise ethylcellulose and a pharmaceutically acceptable plasticizer.

22. The pharmaceutical composition of claim 17, wherein the first sustained release layer comprises ethylcellulose and a pharmaceutically acceptable plasticizer, and the second sustained release layer is not present.

23. The pharmaceutical composition of claim 17, wherein the optional sealing layer is present and comprises hydroxypropylmethyl cellulose.

24. The pharmaceutical composition of claim 17, wherein the weakly basic, poorly soluble drug in the timed pulsatile release and rapid release beads comprises ondansetron, or a pharmaceutically acceptable salt, solvate, and/or ester thereof.

25. The pharmaceutical composition of claim 17, wherein:
the timed pulsatile release particles each comprise:
   the organic acid layer comprises fumaric acid and hydroxypropyl cellulose;
   the first sustained release layer comprises ethylcellulose and a first pharmaceutically acceptable plasticizer;
   the drug layer comprises hydroxypropyl cellulose, and ondansetron or a pharmaceutically acceptable salt, solvate and/or ester thereof;
   the optional sealing layer is present and comprises hydroxypropylmethyl cellulose;
   the timed pulsatile release layer comprises ethylcellulose, hydroxypropylmethylcellulose phthalate, and a second pharmaceutically acceptable plasticizer;
the rapid release particles each comprise a granulate comprising:
   ondansetron or a pharmaceutically acceptable salt, solvate and/or ester thereof;
   fumaric acid;
   lactose;
   microcrystalline cellulose; and
   crospovidone.

26. The pharmaceutical composition of claim 25, wherein the first and second pharmaceutically acceptable plasticizers are independently selected from the group consisting of triacetin, tributyl citrate, triethyl citrate, acetyl tri-n-butyl citrate, diethyl phthalate, dibutyl sebacate, polyethylene glycol, polypropylene glycol, castor oil, acetylated mono- and diglycerides and mixtures thereof.

27. The pharmaceutical composition of claim 26, wherein the first and second pharmaceutically acceptable plasticizers are both triethyl citrate, and the second sustained release layer is not present.

28. A capsule comprising the pharmaceutical composition of claim 1.

29. A capsule comprising the pharmaceutical composition of claim 27.

30. A method of treating emesis comprising administering the pharmaceutical composition of claim 1 to a patient in need thereof.

31. The method of claim 30, wherein said administering is once-a-day.

32. A method of treating emesis comprising administering the pharmaceutical composition of claim 27 to a patient in need thereof.

33. The method of claim 32, wherein said administering is once-a-day.

34. The pharmaceutical composition of claim 24 wherein the weakly basic, poorly soluble drug in the timed pulsatile release and rapid release beads comprises ondansetron hydrochloride.

35. The pharmaceutical composition of claim 25 wherein the rapid release particles each comprise a granulate comprising:
   ondansetron hydrochloride;
   fumaric acid;
   lactose;
   microcrystalline cellulose; and
   crospovidone.

* * * * *